United States Patent
Deem et al.

(10) Patent No.: US 8,974,462 B2
(45) Date of Patent: Mar. 10, 2015

(54) DEVICES AND METHODS FOR MINIMALLY INVASIVE ACCESS INTO A JOINT

(75) Inventors: Mark Deem, Mountain View, CA (US); Michael Hendricksen, Redwood City, CA (US); Darin Gittings, Sunnyvale, CA (US); Mark Hirotsuka, San Jose, CA (US); Paritosh Ambekar, Fremont, CA (US); J. Brook Burley, Mountain View, CA (US); William Kaiser, San Jose, CA (US); James Flom, San Carlos, CA (US)

(73) Assignee: Pivot Medical, Inc., Sunnyvale, CA (US)

( * ) Notice: Subject to any disclaimer, the term of this patent is extended or adjusted under 35 U.S.C. 154(b) by 538 days.

(21) Appl. No.: 12/862,701

(22) Filed: Aug. 24, 2010

(65) Prior Publication Data

US 2011/0166579 A1    Jul. 7, 2011

Related U.S. Application Data

(63) Continuation-in-part of application No. 12/483,446, filed on Jun. 12, 2009, which is a continuation-in-part of application No. 12/726,268, filed on Mar. 17, 2010.

(60) Provisional application No. 61/061,457, filed on Jun.

(Continued)

(51) Int. Cl.
*A61B 17/58* (2006.01)
*A61B 17/60* (2006.01)
(Continued)

(52) U.S. Cl.
CPC ........... *A61B 17/025* (2013.01); *A61B 17/3421* (2013.01); *A61B 2017/00115* (2013.01); *A61B 2017/00557* (2013.01); *A61B 2017/00946* (2013.01); *A61B 2017/0212* (2013.01); *A61B 2017/0275* (2013.01); *A61B 2017/320048* (2013.01); *A61B 2017/3488* (2013.01); (Continued)

(58) Field of Classification Search
USPC ........ 606/90, 89, 91, 192, 195; 623/22.11, 22
See application file for complete search history.

(56) References Cited

U.S. PATENT DOCUMENTS 3,840,014 A   10/1974   Ling et al.
3,875,595 A    4/1975   Froning
(Continued)

FOREIGN PATENT DOCUMENTS

DE    25 01 080    7/1976
EP    0 507 645    10/1992
(Continued)

OTHER PUBLICATIONS

Byrd, Operative Hip Arthroscopy, 2005, 146-147.
(Continued)

*Primary Examiner* — David Bates
*Assistant Examiner* — Samuel Hanna
(74) *Attorney, Agent, or Firm* — Pandiscio & Pandiscio

(57) ABSTRACT

Devices and methods are disclosed for providing access to a central compartment of a hip joint. The devices can access the central compartment by distracting all or a portion of the labrum. The labrum can be distracted by advancing a device underneath the bottom edge of the labrum, and using the device to further distract the labrum. Some devices can move underneath the labrum to provide a gap for other devices to access the central compartment.

5 Claims, 19 Drawing Sheets

Related U.S. Application Data 13, 2008, provisional application No. 61/164,604, filed on Mar. 30, 2009, provisional application No. 61/210,315, filed on Mar. 17, 2009, provisional application No. 61/268,340, filed on Jun. 11, 2009, provisional application No. 61/278,744, filed on Oct. 9, 2009, provisional application No. 61/336,284, filed on Jan. 20, 2010, provisional application No. 61/236,497, filed on Aug. 24, 2009.

(51) Int. Cl.
*A61F 2/00* (2006.01)
*A61B 17/02* (2006.01)
*A61B 17/34* (2006.01)
*A61F 5/04* (2006.01)
*A61M 25/10* (2013.01)
*A61B 17/00* (2006.01)
*A61B 17/32* (2006.01)
*A61B 19/00* (2006.01)
*A61M 25/00* (2006.01)
*A61M 25/01* (2006.01)
*A61M 27/00* (2006.01)

(52) U.S. Cl.
CPC ........... *A61B2019/4889* (2013.01); *A61F 5/04* (2013.01); *A61M 25/0045* (2013.01); *A61M 25/0068* (2013.01); *A61M 25/0102* (2013.01); *A61M 25/10* (2013.01); *A61M 25/1002* (2013.01); *A61M 27/00* (2013.01); *A61M 2025/0004* (2013.01); *A61M 2025/0081* (2013.01); *A61M 2025/0175* (2013.01); *A61M 2025/1072* (2013.01); *A61M 2210/02* (2013.01)
USPC .............................. 606/90; 606/192; 606/195

(56) References Cited

U.S. PATENT DOCUMENTS

| | | | |
|---|---|---|---|
| 4,467,479 A | 8/1984 | Brody | |
| 4,669,106 A | 5/1987 | Ammerman | |
| 4,772,266 A | 9/1988 | Groshong | |
| 4,874,375 A | 10/1989 | Ellison | |
| 4,928,670 A | 5/1990 | DeLorenzo | |
| 4,968,316 A | 11/1990 | Hergenroeder | |
| 4,983,165 A | 1/1991 | Loiterman | |
| 4,995,875 A | 2/1991 | Coes | |
| 5,019,042 A | 5/1991 | Sahota | |
| 5,071,410 A | 12/1991 | Pazell | |
| 5,171,297 A | 12/1992 | Barlow et al. | |
| 5,176,683 A | 1/1993 | Kimsey et al. | |
| 5,213,112 A | 5/1993 | Niwa et al. | |
| 5,234,455 A | 8/1993 | Mulhollan | |
| 5,290,220 A | 3/1994 | Guhl | |
| 5,342,386 A | 8/1994 | Trotta | |
| 5,344,459 A | 9/1994 | Swartz | |
| 5,411,475 A | 5/1995 | Atala et al. | |
| 5,411,517 A | 5/1995 | Guignard | |
| 5,704,372 A | 1/1998 | Moll et al. | |
| 5,725,545 A | 3/1998 | Bircoll | |
| 5,738,629 A | 4/1998 | Moll et al. | |
| 5,803,902 A | 9/1998 | Sienkiewicz et al. | |
| 5,817,123 A | 10/1998 | Kieturakis et al. | |
| 5,820,595 A * | 10/1998 | Parodi ....................... | 604/101.05 |
| 5,827,289 A | 10/1998 | Reiley et al. | |
| 5,827,318 A | 10/1998 | Bonutti | |
| 5,888,220 A | 3/1999 | Felt et al. | |
| 6,017,305 A | 1/2000 | Bonutti | |
| 6,123,718 A | 9/2000 | Tu et al. | |
| 6,171,236 B1 | 1/2001 | Bonutti | |
| 6,187,023 B1 | 2/2001 | Bonutti | |
| 6,217,548 B1 | 4/2001 | Tsugita et al. | |
| 6,468,289 B1 | 10/2002 | Bonutti | |
| 6,482,209 B1 | 11/2002 | Engh et al. | |
| 6,575,979 B1 | 6/2003 | Cragg | |
| 6,616,673 B1 | 9/2003 | Stone et al. | |
| 6,620,181 B1 | 9/2003 | Bonutti | |
| 6,855,149 B2 | 2/2005 | Dye | |
| 6,859,661 B2 | 2/2005 | Tuke | |
| 6,860,892 B1 | 3/2005 | Tanaka et al. | |
| 7,166,121 B2 | 1/2007 | Reiley et al. | |
| 7,189,229 B2 | 3/2007 | Lopath et al. | |
| 7,201,756 B2 | 4/2007 | Ross et al. | |
| 7,216,385 B2 | 5/2007 | Hill | |
| 7,217,273 B2 | 5/2007 | Bonutti | |
| 7,226,462 B2 | 6/2007 | Tanaka et al. | |
| 7,241,303 B2 | 7/2007 | Reiss et al. | |
| 7,300,448 B2 | 11/2007 | Criscuolo et al. | |
| 7,488,337 B2 | 2/2009 | Saab et al. | |
| 8,491,567 B2 | 7/2013 | Magnin et al. | |
| 2001/0001128 A1 | 5/2001 | Holman et al. | |
| 2001/0001315 A1 | 5/2001 | Bates et al. | |
| 2002/0177866 A1 | 11/2002 | Weikel et al. | |
| 2003/0004460 A1 | 1/2003 | Bedell | |
| 2003/0033017 A1 | 2/2003 | Lotz et al. | |
| 2003/0220698 A1 | 11/2003 | Mears et al. | |
| 2004/0059290 A1 | 3/2004 | Palasis | |
| 2004/0098015 A1 | 5/2004 | Weikel et al. | |
| 2004/0106861 A1 | 6/2004 | Leitner | |
| 2004/0116848 A1 | 6/2004 | Gardeski et al. | |
| 2004/0138754 A1 | 7/2004 | Lang et al. | |
| 2004/0236342 A1 | 11/2004 | Ferree et al. | |
| 2004/0249360 A1 | 12/2004 | Spehalski | |
| 2005/0267482 A1 | 12/2005 | Hyde, Jr. | |
| 2006/0015171 A1 | 1/2006 | Armstrong | |
| 2006/0184246 A1 | 8/2006 | Zwirkowski | |
| 2006/0259063 A1 | 11/2006 | Bates et al. | |
| 2006/0293685 A1 * | 12/2006 | Stone et al. ..................... | 606/90 |
| 2006/0293750 A1 | 12/2006 | Sherman et al. | |
| 2007/0173946 A1 | 7/2007 | Bonutti | |
| 2007/0213759 A1 | 9/2007 | Osborne et al. | |
| 2007/0219561 A1 | 9/2007 | Lavallee et al. | |
| 2007/0255394 A1 | 11/2007 | Ryan | |
| 2007/0265635 A1 | 11/2007 | Torrie et al. | |
| 2007/0288095 A1 | 12/2007 | Wirtel et al. | |
| 2008/0019004 A1 | 1/2008 | Hansen | |
| 2008/0045967 A1 | 2/2008 | Lubinus et al. | |
| 2008/0109004 A1 | 5/2008 | Da Rold et al. | |
| 2009/0112214 A1 * | 4/2009 | Philippon et al. ............... | 606/90 |
| 2009/0299282 A1 | 12/2009 | Lau et al. | |
| 2009/0312807 A1 | 12/2009 | Boudreault et al. | |
| 2010/0312179 A1 | 12/2010 | Nikolchev et al. | |

FOREIGN PATENT DOCUMENTS

| | | |
|---|---|---|
| FR | 1 061 009 | 4/1954 |
| FR | 2 734 146 | 11/1996 |
| WO | WO 92/22259 | 12/1993 |
| WO | WO 97/27897 | 8/1997 |
| WO | WO 99/59669 | 11/1999 |
| WO | WO 00/23009 | 4/2000 |
| WO | WO 01/45601 | 6/2001 |
| WO | WO 2005/048812 | 6/2005 |
| WO | WO 2007/080454 | 7/2007 |
| WO | WO 2007/092841 | 8/2007 |
| WO | WO 2009/042429 | 4/2009 |
| WO | WO 2009/152470 | 12/2009 |
| WO | WO 2010/097724 | 2/2010 |
| WO | WO 2010/107949 | 9/2010 |
| WO | WO 2012/064786 | 5/2012 |

OTHER PUBLICATIONS

Ganz et al., Surgical dislocation of the adult hip, The Journal Of Bone and Joint Surgery, Nov. 2001, vol. 83-B, No. 8, 1119-1124.
Aydin et al., A New Noninvasive Controlled Intra-articular Ankle Distraction Technique on a Cadaver Model, Arthroscopy: The Journal of Arthroscopic and Related Surgery, Aug. 2006. vol. 22, No. 8, 905.e1-905.e3.
Burman, Arthroscopy Or The Direct Visualization Of Joints: An Experimental Cadaver Study, The Journal Of Bone And Joint Surgery, Oct. 1931, vol. XIII, No. 4, 669-695.

(56) References Cited

OTHER PUBLICATIONS

Dienst, Chapter 11: Hip Arthroscopy Without Traction, 2005, pp. 170 and 174.

Dienst et al., Hip Arthroscopy Without Traction: In Vivo Anatomy Of The Peripheral Hip Joint Cavity, Arthroscopy: The Journal of Arthroscopic and Related Surgery, Nov.-Dec. 2001, vol. 17, No. 9, 924-931.

Sartoretti et al., Angioplasty Balloon Catheters Used for Distraction of the Ankle Joint, Arthroscopy: The Journal Of Arthroscopic And Related Surgery, Feb. 1996, vol. 12, No. 1, 82-86.

Shetty et al., Hip arthroscopy: current concepts and review of literature, Br J Sports Med, 2007, 41, 64-68.

Tan et al., Contribution Of Acetabular Labrum To Articulating Surface Area And Femoral Head Coverage In Adult Hip Joints; An Anatomic Study In Cadavera, The American Journal of Orthopedios, Nov. 2001, vol. XXX, No. 11, 809-812.

Dienst et al., Effects of Traction, Distension, and Joint Position on Distraction of the Hip Joint. An Experimental Study in Cadavers, Arthrosoopy: The Journal of Arthroscopic and Related Surgery, Oct. 2002, vol: 18. No. 8, 865-871.

\* cited by examiner

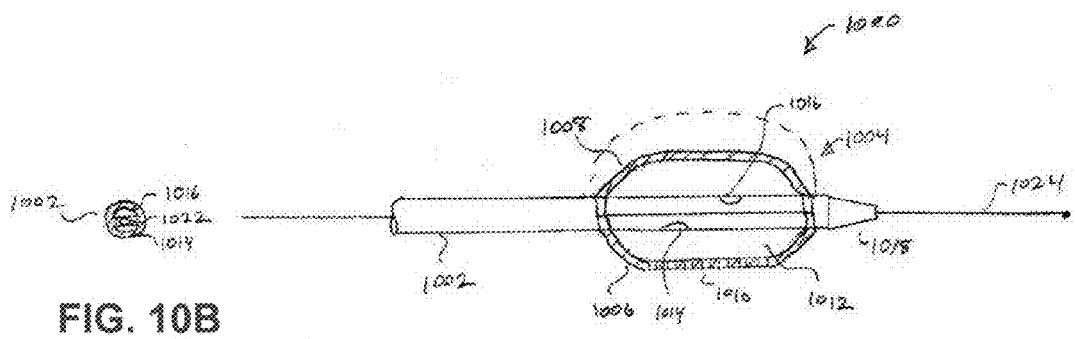
FIG. 10B
FIG. 10A
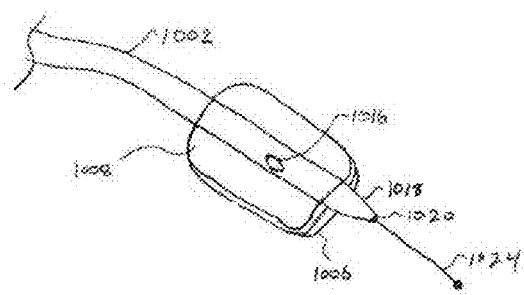
FIG. 10C

DEVICES AND METHODS FOR MINIMALLY INVASIVE ACCESS INTO A JOINT

REFERENCE TO PENDING PRIOR PATENT APPLICATIONS

This patent application:

(i) is a continuation-in-part of pending prior U.S. patent application Ser. No. 12/483,446, filed Jun. 12, 2009 by David Boudreault et al. for METHOD AND APPARATUS FOR JOINT DISTRACTION, which patent application in turn claims benefit of (a) U.S. Provisional Patent Application Ser. No. 61/061,457, filed Jun. 13, 2008, and (b) U.S. Provisional Patent Application Ser. No. 61/164,604, filed Mar. 30, 2009;

(ii) is a continuation-in-part of pending prior
U.S. patent application Ser. No. 12/726,268, filed Mar. 17, 2010 by Julian Nikolchev et al. for METHOD AND APPARATUS FOR DISTRACTING A JOINT, INCLUDING THE PROVISION AND USE OF A NOVEL JOINT-SPACING BALLOON CATHETER AND A NOVEL INFLATABLE PERINEAL POST, which patent application claims benefit of (a) U.S. Provisional Patent Application Ser. No. 61/210,315, filed Mar. 17, 2009, (b) U.S. Provisional Patent Application Ser. No. 61/268,340, filed Jun. 11, 2009, (c) U.S. Provisional Patent Application Ser. No. 61/278,744, filed Oct. 9, 2009, and (d) U.S. Provisional Patent Application Ser. No. 61/336,284, filed Jan. 20, 2010; and (iii) claims benefit of pending prior U.S. Provisional Patent Application Ser. No. 61/236,497, filed Aug. 24, 2009 by Mark Deem et al. for DEVICES AND METHODS FOR MINIMALLY INVASIVE ACCESS INTO A JOINT.

The nine (9) above-identified patent applications are hereby incorporated herein by reference.

FIELD OF THE INVENTION

The present invention relates to medical devices and methods for accessing a joint, and more specifically to devices and methods for providing minimally invasive access into the central compartment of a hip joint.

BACKGROUND OF THE INVENTION

Obtaining arthroscopic access into orthopedic joints to perform surgical procedures can be extremely challenging. This is particularly true of the hip joint, which has two tissue barriers that must be crossed in order to gain access to the inner part of the joint. The outer barrier is known as the capsule, a series of tight overlapping ligaments surrounding the joint. The area within the capsule is known as the peripheral compartment.

Within the peripheral compartment, the joint is fluidly sealed by a skirt-like tissue known as the labrum which is attached to the acetabular rim and hugs tightly around the base of the femoral head. The labrum/femoral head interface creates a vacuum seal within the joint which helps to hold the femoral head tightly within the acetabulum. In order to gain access to the central compartment (i.e., the portion of the joint within the labrum lying between the femoral head and acetabulum), the seal of the labrum must be broken and instruments then introduced into the very narrow opening between the bottom edge of the labrum and femoral head.

In arthroscopic surgery, access to the peripheral compartment is typically obtained through the use of elongated tubular devices (e.g., arthroscopic portals or cannulas) which are inserted through the patient's skin and through the ligaments of the capsule so as to provide a tunnel or lumen through which instruments may be introduced. Two to three such portals are typically employed, one being used for placement of an arthroscope and the remaining portal(s) being available for the introduction of other instruments.

In order to gain access to the central compartment, surgeons typically use a distraction table, a surgical table that includes a post placed against the patient's perineum and a tensioning device which fastens to the patient's foot or ankle and allows high forces to be exerted on the patient's leg to distract the femur and create space within the joint. However, these tables are not only large, cumbersome and expensive, but they limit the mobility of the joint during the procedure and frequently produce complications such as nerve damage.

Methods and devices have been proposed for distracting the hip joint without using a distraction table. For example, commonly assigned U.S. patent application Ser. No. 12/483,446, filed Jun. 12, 2009, entitled "Methods and Apparatus for Joint Distraction", the entirety of which is incorporated by reference herein, and U.S. patent application Ser. No. 12/726,268, filed Mar. 17, 2010, the entirety of which is incorporated by reference herein, disclose various internal distraction devices for distracting the hip and other joints. These devices use balloons or other expandable features placed within the central compartment to displace the femoral head further away from the acetabulum in order to allow access for surgical instruments. While such devices eliminate the need for a distraction table, challenges may still be encountered when introducing these devices into the peripheral and central compartments. Further, even where a conventional distraction table is used, the placement of portals and the introduction of instruments into the peripheral and central compartments remain challenging.

BRIEF SUMMARY OF THE INVENTION

An embodiment of the invention provides a method for distracting a femoral head from an acetabulum of a hip joint. A first catheter may be inserted into a central compartment of the hip joint. A first balloon of the first catheter may be inflated to distract the femoral head from the acetabulum a first distance. A second balloon may be advanced over the inflated first balloon. Then the second balloon may be inflated to distract the femoral head from the acetabulum a second distance.

Another embodiment of the invention provides a system for distracting a femoral head from an acetabulum of a hip joint. The system may include a first elongated catheter with a proximal end and a distal end, and a first balloon about the distal end. The system may also include a second elongated catheter with a lumen, and a second balloon. The lumen of the second elongated catheter may be slidably coupled over the first elongated catheter.

Yet another embodiment of the invention provides a method for distracting a femoral head from an acetabulum of a hip joint. An access lumen may be created through the femoral head, the access lumen communicating with central compartment of a hip joint. A portion of a distraction catheter may be inserted through the access lumen and into the central compartment of the hip joint. Then the head of the femur may be distracted from the acetabulum using the distraction catheter.

Yet another embodiment of the invention provides a method for distracting a femoral head from an acetabulum of a hip joint. A device with a concave lower surface and a convex upper surface may be inserted under a labrum and into a central compartment of the hip joint. Then the femoral head may be distracted from the acetabulum using the device.

Yet another embodiment of the invention provides a device for distracting a femoral head from an acetabulum of a hip joint. The device may include an elongated member with a proximal end and a distal end. A spoon member with a concave and a convex surface may be disposed at the distal end of the elongated member. A balloon may be coupled to the concave surface.

Yet another embodiment of the invention provides a method for providing access to a central compartment of the hip joint. A blade extending distally from a tip of a cannula device may be inserted under a labrum of the hip joint. A beveled distal surface of the cannula device may be further advanced under the labrum such that the labrum rests over an outer wall of the cannula and a distal opening of the cannula is within the central compartment. The cannula may be maintained in place so that other devices can access the central compartment via the lumen.

Yet another embodiment of the invention provides a cannula for providing access to a central compartment of the hip joint. The cannula may include an elongated shaft with a proximal end, a distal end, and lumen. The distal end may include a beveled portion, and a blade portion shaped to lever a labrum from the femoral head.

Yet another embodiment of the invention provides a method for providing access to a central compartment a hip joint. The femur may be moved out of a first position to expose more of a femoral neck and head. A device may be placed on the exposed portion of the femoral neck and head and abutting a labrum. Then the femur may be moved back into the first position to move the device underneath the labrum and create a gap between the labrum and the femoral head.

Yet another embodiment of the invention provides a device for providing access to a central compartment a hip joint. The device may include an elongated flexible shaft. An expansion device may be coupled to the elongated flexible shaft. The expansion device may include an adhering surface for adhering to a femoral neck and head.

Yet another embodiment of the invention provides a method for providing access to a central compartment a hip joint. The femur may be moved out of a first position to expose more of a femoral neck and head. A device may be placed on the exposed portion of the femoral neck and head and abutting a labrum. The femur may be moved back into the first position to move the device underneath the labrum and create a gap between the labrum and the femoral head. The device may be inflated to distract the femoral head from an acetabulum. A guidewire may be advanced through the device and past an acetabular fossa of the acetabulum. Then the device may be removed while leaving the guidewire in place.

Yet another embodiment of the invention provides a device for providing access to a central compartment a hip joint. The device may include an elongated flexible shaft having a guidewire lumen, an inflation lumen, and a suction lumen. A suction chamber may be fluidly connected to the suction lumen, and may have a bottom surface with a plurality of suction ports. A balloon chamber may be fluidly connected to the inflation lumen. The balloon chamber may have a balloon. The balloon may have an inflated profile with a convex outer surface. A distalmost wedged tip may be connected to the flexible shaft.

In another form of the invention, there is provided a method for creating space within a joint of the type comprising a bone head received within a bone socket, the method comprising:

inserting an elongated hollow structure into the space between the bone head and the bone socket; and introducing fluid under pressure into the space between the bone head and the bone socket so as to displace the bone head from the bone socket.

These and other embodiments are described in further detail in the following description, which is to be considered together with the following figures.

BRIEF DESCRIPTION OF THE DRAWINGS

FIG. 10A is a partial cross-sectional view of a device for providing access to a central compartment of a hip joint, according to an embodiment of the invention.

FIGS. 10B and 10C are cross-sectional and perspective views, respectively, of the device shown in FIG. 10A.

DETAILED DESCRIPTION OF THE INVENTION

Devices and methods are disclosed regarding accessing the central compartment of a hip joint. The devices disclosed herein can be generally used after access has been established into the capsule (i.e., the peripheral compartment) of a hip joint, and before access into the central compartment has been established. Two to three portals may be established which penetrate a patient's skin and the capsule. The devices disclosed herein can use these portals to gain further access to the central compartment. However, the devices of the invention may also be useful for peripheral compartment access as well as access into other joints such as the shoulder, knee, or ankle.

Devices disclosed herein can access the central compartment of the hip, or provide access to the central compartment for other devices, without cutting or damaging the labrum. Access to the central compartment is generally obtained by inserting a small profile device underneath the labrum and creating a small gap between the labrum and the femoral head. The device can then facilitate distraction of the labrum from the femoral head and/or distraction of the acetabulum from the femoral head, for example, by increasing the size of the gap between the labrum and the femoral head and/or by providing access to other distraction devices. Other distraction devices can include balloon catheters such as those disclosed in the previously incorporated U.S. patent application Ser. Nos. 12/483,446 and 12/726,268. The devices and methods disclosed herein may be used in a minimally invasive manner in conjunction with known arthroscopic visualization systems and/or other visualization systems such as fluoroscopy.

Figure 1:
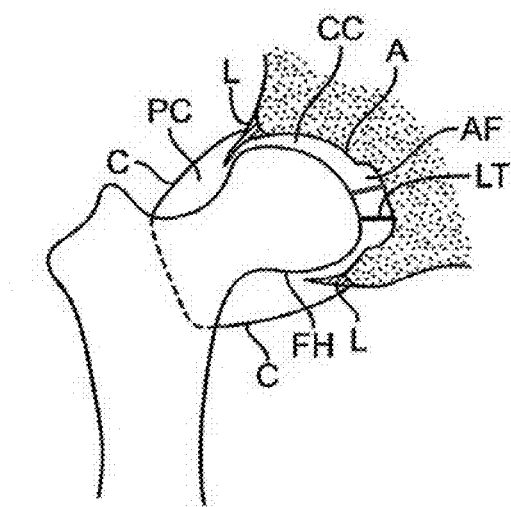
FIG. 1 is a simplified cross-sectional view of a hip joint in the anterior posterior (AP) plane.

FIG. 1 illustrates the basic anatomy of a hip joint. The hip joint is formed between the head of the femur FH and the acetabulum A, a concave surface of the pelvis. The acetabular fossa AF is a recessed region in the acetabulum. A blanket of ligaments covers the joint, forming a capsule C. Additionally the acetabular labrum L, a fibrocartilaginous lip, surrounds the head of the femur, deepens the joint pocket and increases the surface area of contact. The labrum L divides the hip joint into two compartments within the joint capsule: a central compartment CC and a peripheral compartment PC. The central compartment CC is within the confines of the labrum L and contains the majority of the joint cartilage and the ligamentum teres LT, a ligament attached to a depression in the acetabulum (the acetabular notch or fossa AF) and a depression on the femoral head (the fovea of the head). The peripheral compartment PC is generally considered to be everything outside the labrum and within the capsular ligaments C. The central compartment CC is generally not visible until the joint has been distracted.

Figure 2:
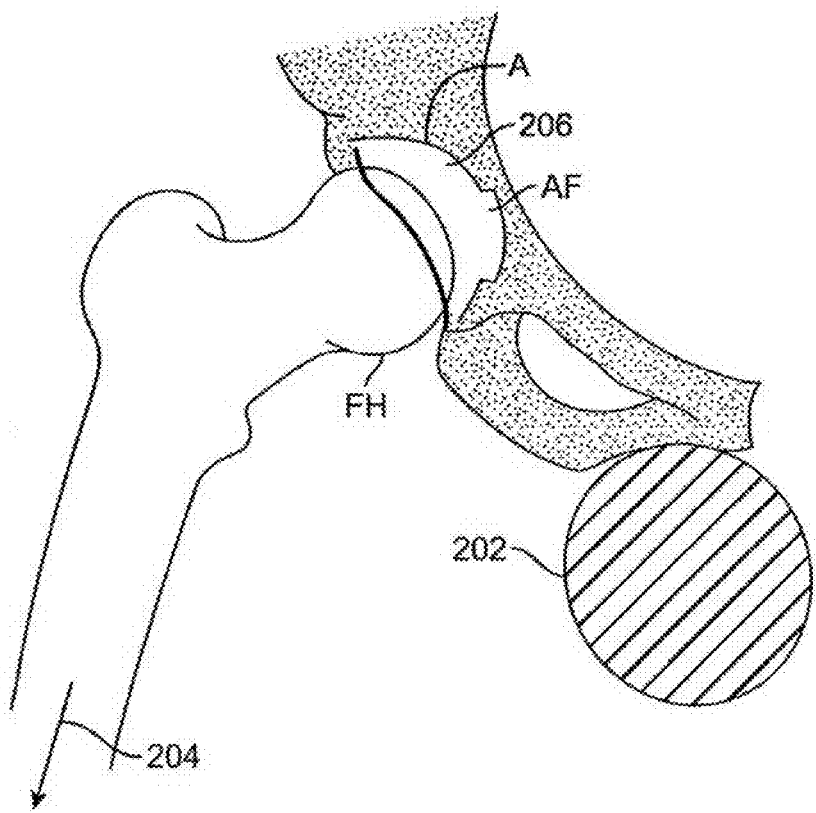
FIG. 2 is a simplified cross-sectional view of a hip joint undergoing a prior art method for distracting a femoral head from an acetabulum (top view).

FIG. 2 illustrates how traction 204 is conventionally applied to the patient's leg and against a post 202 positioned against the perineum region to distract the femoral head FH away from the acetabulum A, thereby creating a space 206 between the two joint surfaces. This space 206 allows a surgeon to access the joint and perform diagnostic or therapeutic procedures. However, conventional distraction tables are often rigid systems affixed to an operating room table and they are not easily adjustable. Thus, once distraction is obtained, conventional distraction tables are locked into position to maintain the distraction and have very limited capability for any further manipulation of the joint in order to provide greater access to the joint or access to different regions of the joint space. For example, in the case of a hip joint, it would be desirable to be able to flex, extend, abduct, adduct, laterally rotate or medially rotate the joint through a broad range of motion so that access and visibility to the joint space and adjacent structures may be adjusted while the joint is distracted. In addition, even with distraction tables that allow some manipulation of the hip joint, because traction must be maintained, it is not possible to bend the patient's knee using conventional distraction tables. When the leg is straight, the hip joint may be flexed up to approximately 20°, but bending the knee allows the hip joint to be flexed even more, thereby allowing even greater access to the joint. Additionally, the pressure exerted by the post 202 against the perineum can result in post-operative complications (e.g., nerve trauma) that would desirably be avoided.

Figure 3:
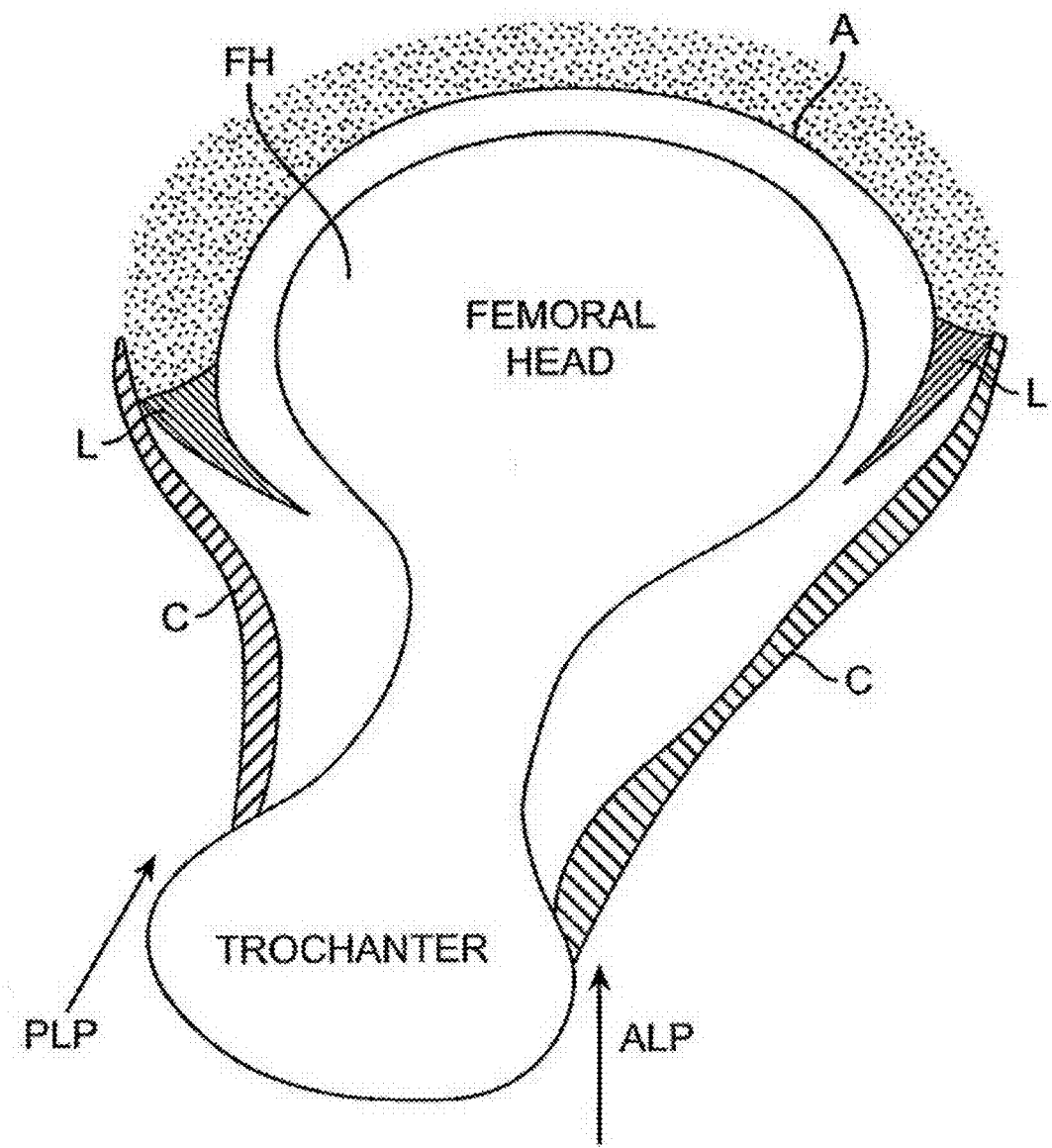
FIG. 3 is a simplified cross-sectional view of a hip joint.

FIG. 3 illustrates some of the possible entry portals for delivering instruments into the hip joint. FIG. 3 is a top view of a hip joint in which the femoral head FH rests against the acetabulum A. The joint space is covered by the capsule C and the labrum L. Access into the joint may be obtained by introducing instruments through a posterolateral portal PLP along the lateral side of, and posterior to, the joint, or an anterolateral portal ALP along a side of, and anterior to, the joint.

Figure 4A:
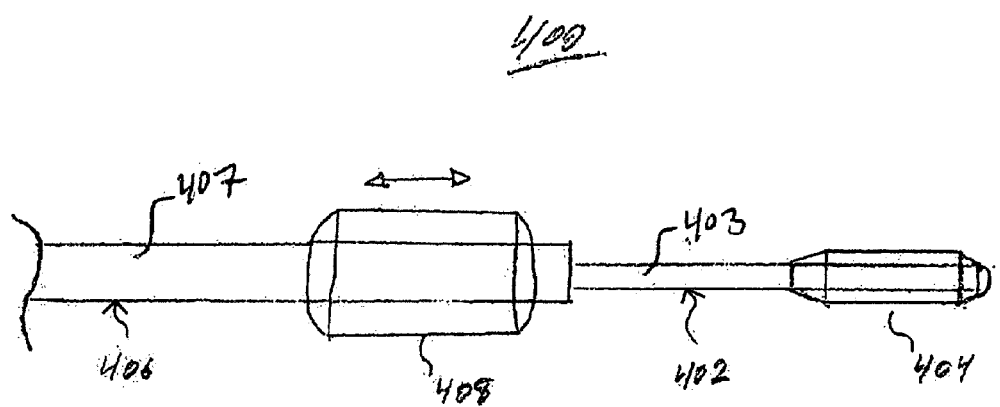
FIG. 4A is a side view of a system for distracting a femoral head from an acetabulum, according to an embodiment of the invention.

FIG. 4A shows a side view of a system 400 for distracting a femoral head from an acetabulum of a hip joint. The balloon of system 400 (see below) and related instruments may be delivered into the joint space through a port or cannula, or using minimally invasive techniques such as Seldinger-like or percutaneous introduction, or a open cutdown procedure with larger incision may be used.

System 400 includes an elongated catheter 402 having a flexible shaft 403 with a balloon 404 attached to the distal end thereof. The elongated catheter 402 also includes a proximal end (not shown) which includes provisions for coupling to an inflation device, such as a syringe or angioplasty balloon inflation device. The balloon 404 may be constructed from a non-compliant (e.g., 0-10% compliance range) thin-walled material such as PET, or from a semi-compliant (e.g., 10-20% compliance range) thin-walled material, such as PET, nylon, and polyurethane. The balloon may be capable of withstanding high pressures (e.g., up to 800 psi), and include reinforcement features, such as integrated woven fibers, to help prevent bursting of the balloon. The balloon 404 can have a wall thickness ranging from, for example, 0.0001-0.006 inch, and may also have multiple layered wall, e.g. 2-ply or 3-ply, with the layers either adhered to each other or not. The balloon 404 is shown in FIG. 4A in an expanded configuration and may have an expanded diameter of 2-8 mm. The balloon 404 may be folded or collapsed into an unexpanded configuration so as to have an effective diameter which is roughly equivalent to, or slightly larger than, the outer diameter of the shaft 403, which can be approximately 0.5-2 mm. The balloon 404 may utilize various shapes and sizes other than the generally cylindrical shape shown in FIG. 4A, such as spherical, oval, and shapes which are tailored to fit within the acetabulum and the acetabular fossa, such as curved or conical kidney shaped balloons.

The catheter 402 can be constructed using known flexible materials (e.g., extruded polymer tubing) and generally has at least one lumen which is fluidly connected to the balloon 404. The shaft 403 may include a circular profile, or other profiles, such as a triangular, rectangular, oval, or flattened profile, and the catheter 402 may also be configured to be used with a guidewire and have an additional lumen through its length which is open at the distal end, through which the guidewire may be inserted. The distalmost tip of the catheter 402 can be tapered or beveled to a small flattened or pointed shape, preferably made out of a soft polymeric material, or the distalmost tip may be a rounded shape. The catheter 402 may include reinforcing members, such as stainless steel or superelastic alloy, to aid in column strength and pushability. The balloon 404 can be chemically bonded or heat formed to the catheter 402, which may be constructed from the same material as the balloon 404. The balloon 404 and catheter 402 can also include coatings which increase lubricity, such as PTFE. The balloon 404 and catheter 402 can include elements (e.g., metal rings) which are fluoroscopically visible (i.e., radiopaque).

Generally the construction of the catheter 402 and balloon 404 can apply to other balloon catheter embodiments within this disclosure. Further examples of balloons and catheters which can be used throughout this disclosure, either wholly or in combination, are shown in the previously incorporated U.S. patent application Ser. Nos. 12/483,446 and 12/726,268.

System 400 also includes a second catheter 406. The second catheter 406 includes a flexible shaft 407 and a second balloon 408. The second balloon 408 can be configured similarly to balloon 404, however, the second balloon 408 has a larger expanded diameter. The expanded diameter of the second balloon 408 can range in dimension, e.g., from 4-40 mm when the balloon is in an unconstrained condition. The second catheter 406 generally includes an internal lumen which is fluidly connected to the second balloon 404, and also a large main lumen which is configured to be large enough (e.g., 0.5-2 mm) to slide over balloon 404 when deflated and collapsed. The large main lumen may include coatings to increase lubricity, such as PTFE. The second catheter 406 may include a polymer and braided or coiled wire construction to aid in column strength. The second catheter 406 is also flexible and includes a proximal end (not shown) which includes provisions for coupling to a pressure source, such as a hand pump. Other aspects of the second catheter 406 are described in copending U.S. patent application Ser. No. 12/483,446, which has already been incorporated herein by reference.

Figure 4B:
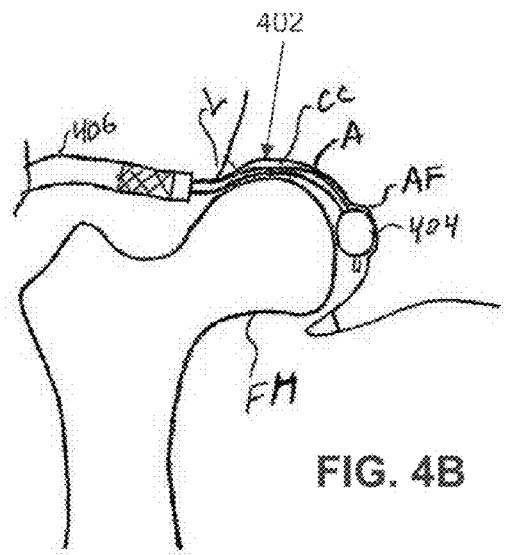
FIGS. 4B-4D are simplified cross-sectional views of a hip joint undergoing a method for distracting a femoral head from an acetabulum, according to an embodiment of the invention.
Figure 4C:
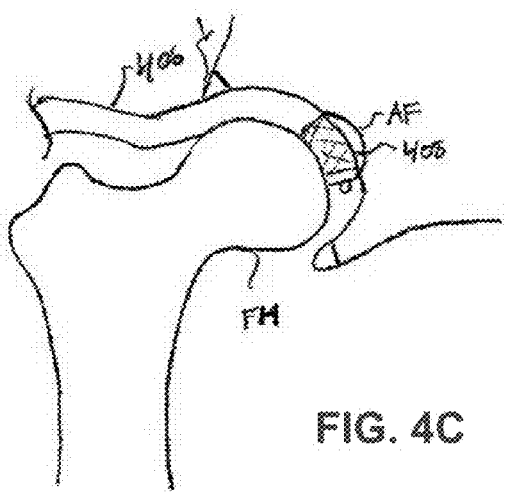
Figure 4D:
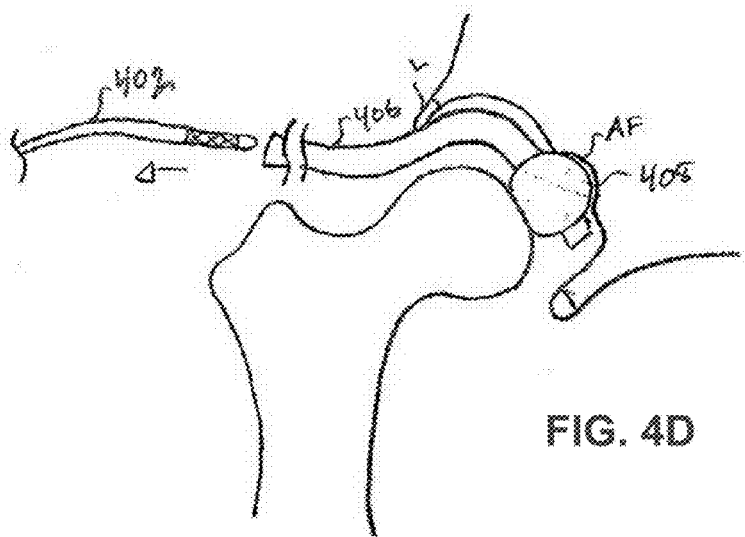

FIGS. 4B-4D show a method for using system 400 to separate the femoral head FH from the acetabulum A.

In FIG. 4B, the elongated catheter 402 has been advanced into the central compartment CC, and the balloon 404 has been inflated in the acetabular fossa AF. Preferably, a guidewire is first advanced under the labrum L into central compartment CC, and catheter 402 (with balloon 404 in its deflated condition) is slidably advanced over the guidewire. The elongated catheter 402 may access the central compartment by pushing the distal tip of the elongated catheter 402 under the labrum L. The elongated catheter 402 preferably has a small distal profile, e.g., a tapered or flattened tip, which can fit beneath the bottom edge of the labrum L. Catheter 402 is then advanced until balloon 404 is in the desired location, e.g., the acetabular fossa AF. The balloon 404 is then inflated to separate the femoral head FH from the acetabulum A by a small first distance, for example, 2-4 mm, and create a gap between the acetabulum and the femoral head FH. The hip joint can also be pressurized with a fluid such as saline to help separate the femoral head FH from the acetabulum A. Alternatively, balloon 404 may be positioned and inflated just beyond (medially) of the acetabular fossa so that it may remain inflated while second balloon 408 is positioned in the fossa AF.

Referring next to FIG. 4C, after the small gap has been created between acetabulum A and the femoral head FH with the first balloon 404, the second catheter 406 (with its balloon 408 deflated) can be slid over the elongated catheter 402 and through the gap into the central compartment CC. The uninflated second balloon 408 is advanced up to the inflated balloon 404. The balloon 404 may be deflated to allow the second balloon 408 to slide over it. Second catheter 406 is advanced to position balloon 408 in the desired location (e.g. acetabular fossa AF).

Referring next to FIG. 4D, the second balloon 408 may then be inflated in the desired location (e.g., within the acetabular fossa AF), which separates the femoral head FH from the acetabulum A by a second distance, for example, 8-12 mm. The balloon 404 of the elongated catheter 402 can then be deflated (if it was not already previously deflated), and the elongated catheter 402 can be removed from the central compartment CC. The inflated second balloon 408 creates a large gap between the femoral head FH and the acetabulum A. Accordingly, other surgical devices may then be introduced under the labrum L into the central compartment CC. Surgical devices may also be inserted through the lumen of the second catheter 406 for access to the central compartment CC.

Figure 5A:
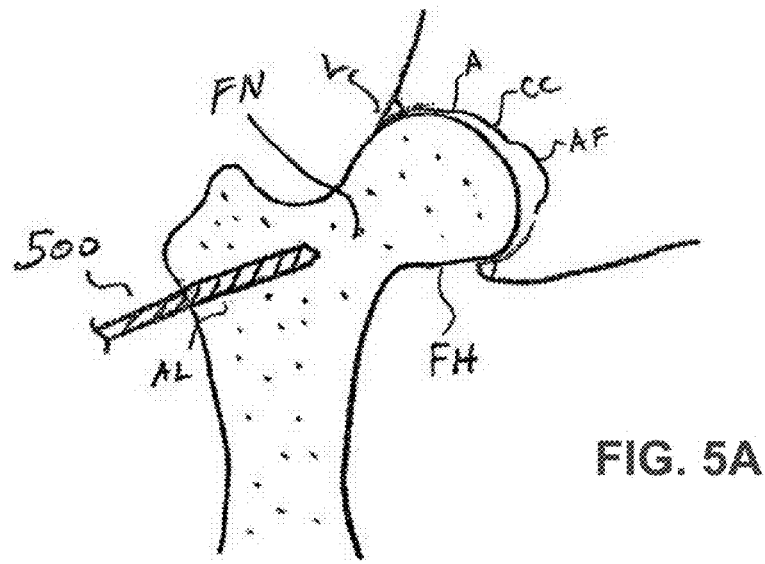
FIGS. 5A and 5B are simplified cross-sectional views of a hip joint undergoing a method for distracting a femoral head from an acetabulum, according to an embodiment of the invention.
Figure 5B:
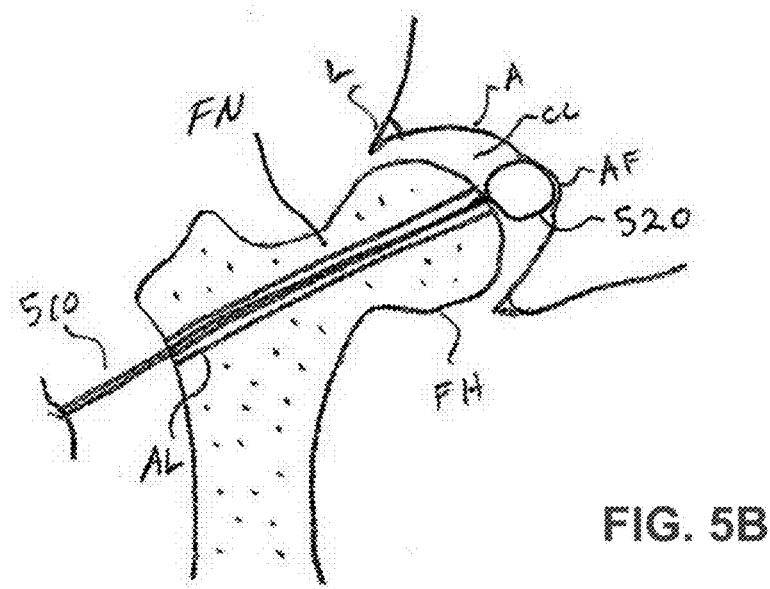

FIGS. 5A and 5B show another method for separating the femoral head FH from the acetabulum A.

FIG. 5A shows a simplified cross-sectional view of an access lumen AL being created in the femoral head FH. The access lumen AL is preferably created parallel to the longitudinal axis of the femoral neck FN. The access lumen AL can be created by drilling the femoral head FH with drill 500. Other drilling techniques known in the art, such as ultrasonic drilling, may also be used. The diameter of the access lumen AL can be, for example, 1-2 mm in diameter. Care should be taken not to damage the articular surface of the acetabulum A when drilling through the femoral head FH. The axis of the access lumen AL preferably aligned to exit at or near the acetabular fossa AF. The access lumen AL provides access to the central compartment CC for a distraction device, such as the balloon catheter 510 shown in FIG. 5B. The balloon catheter 510 can be an elongated catheter with a balloon 520 positioned at a distalmost tip. The balloon catheter 510 can share the general construction of the balloon catheters disclosed herein and in copending U.S. patent application Ser. Nos. 12/483,446 and 12/726,268, which have been incorporated by reference, and balloon 520 preferably has an inflated diameter of 4-40 mm when the balloon is in an unconstrained condition. The balloon catheter 510 can be inserted into the access lumen AL, and inflated at a preferred site (e.g., the acetabular fossa AF) to distract the femoral head FH from the acetabulum A. Other surgical devices can then access the central compartment CC through a gap between the labrum L and the femoral head FH. Alternatively, balloon catheter 510 may have a smaller balloon inflatable to, for example, 2-12 mm which may be used to distract the joint sufficiently to allow introduction of a larger distraction balloon under the labrum and into the central compartment.

Figure 6A:
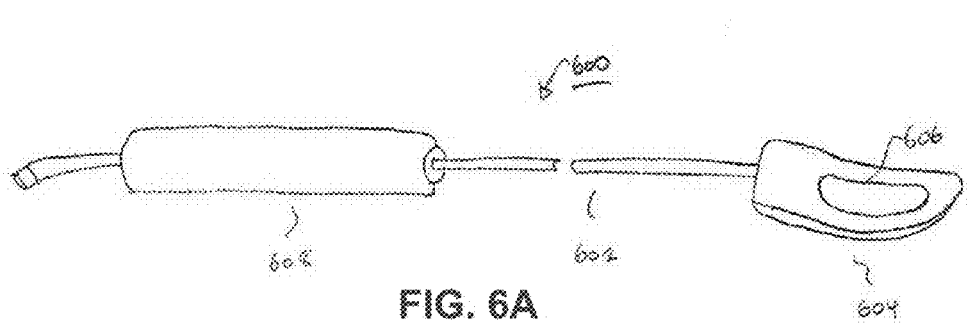
FIG. 6A is a perspective view of a device for distracting a femoral head from an acetabulum, according to an embodiment of the invention.
Figure 6B:
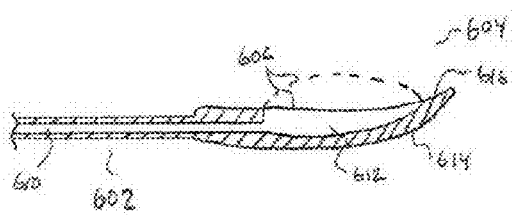
FIGS. 6B and 6C are transverse and axial cross-sectional views, respectively, of portions of the device of FIG. 6A.
Figure 6C:
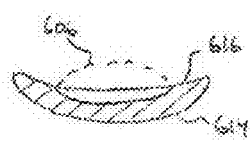

FIGS. 6A-6C show a device 600 for separating the femoral head FH from the acetabulum A.

As shown in FIG. 6A, the device 600 includes a central elongated shaft 602. The distal end of the shaft 602 is coupled to a spoon member 604. The spoon member 604 has a lower convex side and an upper concave side. The concave side includes a balloon 606, which is preferably recessed or even with the rim surface of the concave side when deflated. The spoon member 604 may be formed from a relatively stiff or resiliently flexible metal or polymer, or may be composed all or partially of a softer compliant material to conform to the shape of the femoral head FH and acetabulum A. The spoon member 604 has a distal end with a tapered thickness, creating a wedge-shaped tip configured for sliding under the labrum. The wedge-shaped tip may be a soft polymeric material. A handle 608 is coupled to the proximal end of the shaft 602, and can include a connector for coupling to an inflation device or a pressure source, such as a syringe or hand pump. The shaft 602 can include a lumen fluidly connected to the balloon 606. The shaft 602 may be constructed from a metal or polymer, and may be either rigid, flexible, or malleable.

FIGS. 6B and 6C show cross-sectional views of the distal end of the shaft 602 and spoon member 604. The shaft 602 includes a lumen 610 which is fluidly connected to the interior of balloon 606 and a balloon chamber 612 recessed into spoon member 604. The balloon 606 may expand to a profile as shown by the dashed line. The spoon member 604 includes a convex outer surface 614 and a concave upper surface 616. The concave upper surface 616 can be shaped to match the outer surface of the femoral head FH, while the convex outer surface 614 can be shaped to match the profile of the inner surface of the acetabulum A. Optimally the convex outer surface 614 may be covered with a soft material to reduce trauma on the articular surface.

Figure 6D:
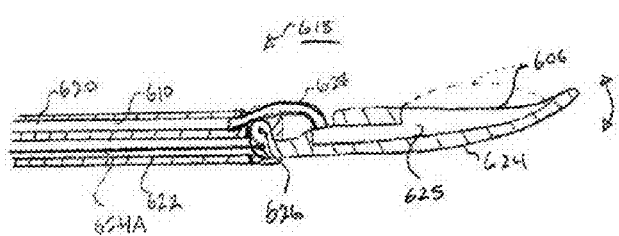
FIG. 6D is an alternative cross-sectional view of a portion of the device of FIG. 6A.

FIG. 6D shows a cross-sectional view of an alternative embodiment of a device 618 for separating the femoral head FH from the acetabulum A. The device 618 is generally configured as the device 600 shown in FIG. 6A but includes an articulating spoon member 624. Shaft 620 includes an additional lumen 622 which houses a slidable push/pull rod 624A. The rod 624A is pivotably connected to spoon member 624, which is pivotably coupled to shaft 620 by a hingepin 626. An inner chamber 625 in spoon member 624 is fluidly coupled to lumen 610 by a flexible hose 628. Balloon 606 is mounted to spoon member 624 to extend over chamber 625. Movement of the push/pull rod 624A within the additional lumen 622 causes the spoon member 624 to pivot about hingepin 626, as shown by the indicative arrows. The handle 608 can include a lever or sliding mechanism to move the push/pull rod 624A.

Figure 6E:
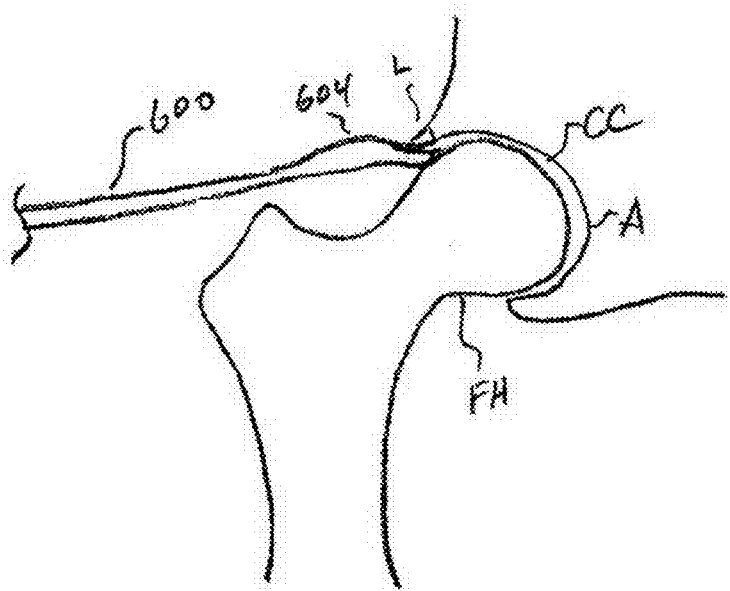
FIGS. 6E-6F are simplified cross-sectional views of a hip joint undergoing a method for distracting a femoral head from an acetabulum, according to an embodiment of the invention.
Figure 6F:
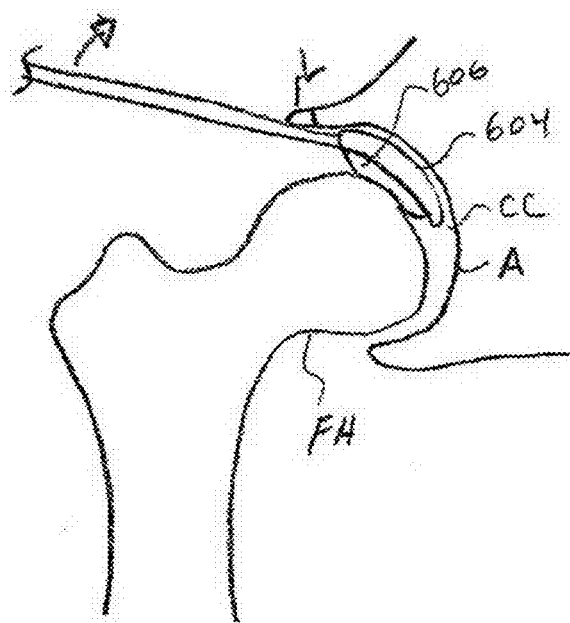

FIGS. 6E and 6F show a method for using device 600, or device 618, to separate the femoral head FH from the acetabulum A.

In FIG. 6E the tapered tip of the spoon member 604 is brought underneath the labrum L, and forcibly slid between the femoral head FH and acetabulum A into the central compartment CC. The concave and convex surfaces of the spoon member 604 preferably conform to match the profiles of the femoral head FH and acetabulum A, respectively, thereby allowing spoon member 604 to be slid underneath the labrum L with relatively low effort. The spoon member 604 may be advanced into the central compartment CC until the balloon 606 is within the central compartment CC.

In FIG. 6F the balloon 606 is inflated to separate the femoral head FH from the acetabulum A. The device 600 may also be used to leverage the femoral head FH from the acetabulum A for additional separation, as shown by the indicative arrow. If device 618 is used, the spoon member 624 may be articulated to provide leverage or to provide better angles of access for the device 618. After the balloon 606 has been inflated, other surgical devices can then access the central compartment CC, or a distraction balloon like that described in copending U.S. patent application Ser. Nos. 12/483,446 and 12/726,268 may be inserted into the joint to distract the joint further.

Figure 7A:
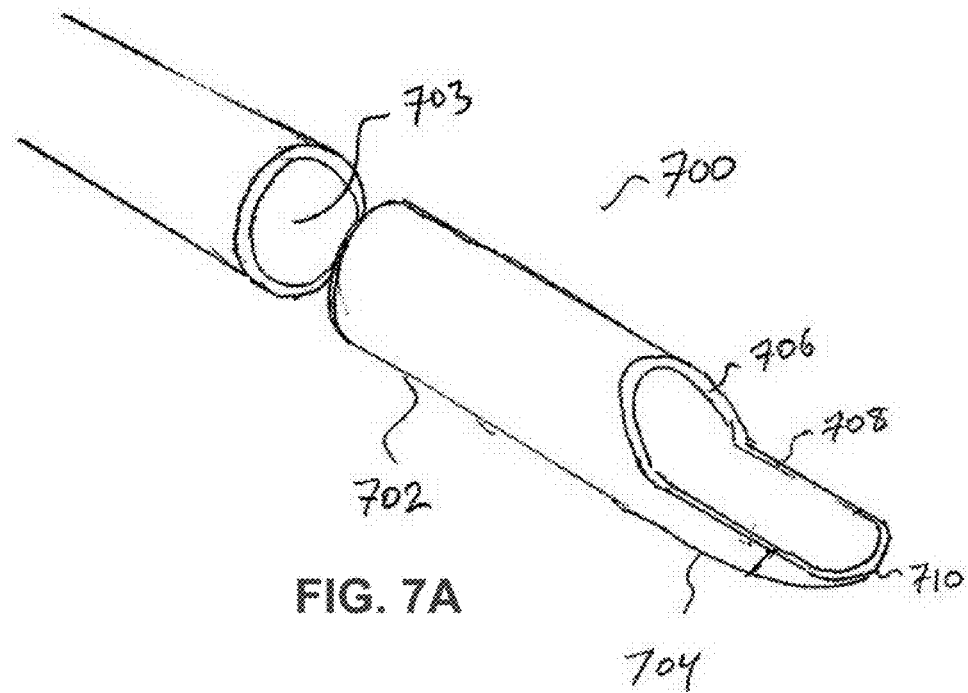
FIG. 7A is a perspective view of a device for providing access to a central compartment of a hip joint, according to an embodiment of the invention.
Figure 7B:
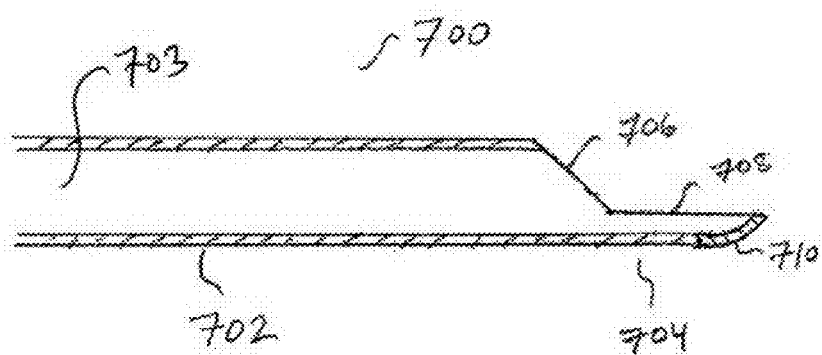
FIG. 7B is a cross-sectional view of the device shown in FIG. 7A.

FIGS. 7A and 7B show a cannula 700 for providing access to the central compartment CC of a hip joint.

Cannula 700 includes a main shaft 702 with a central access lumen 703. The lumen 703 of shaft 702 may be sized to allow passage of other surgical devices, for example, the lumen may be 2-12 mm in diameter. The cannula 700 includes a distal end 704 with a beveled portion 706 and a spoon-like blade 708. The blade 708 may have a curved lower surface and preferably tapers to a small profile flattened tip 710, which may be constructed from a soft polymeric material. Blade 708 preferably has a transverse height or thickness less than about 50%, and more preferably less than about 25%, of the outer diameter of shift 702. The tip preferably has a leading edge of small thickness, for example, less than 1 mm in width. Blade 708 may optionally be pre-shaped, or malleably shapeable, in a curve either upward or downward relative to the longitudinal axis of shaft 702. The cannula 700 may be constructed from a relatively stiff material, such as stainless steel, or from a super-elastic material such as nickel-titanium, or from a plastic or elastomer. The cannula 700 may also be malleable to allow for bending into a preferred shape by a user. The cannula 700 may be thin-walled and have a wall thickness, for example, ranging from 0.005-0.060 inch. Beveled portion 706 has an angle selected to allow it to slide under the labrum without causing damage to it, preferably being in the range of about 10-60° relative to the longitudinal axis of the shaft 702.

Figure 7C:
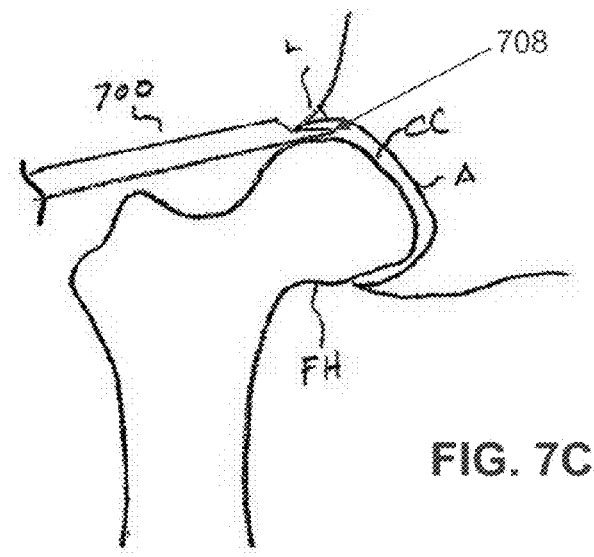
FIGS. 7C-7E are simplified cross-sectional views of a hip joint undergoing a method for accessing a central compartment of a hip joint for distraction of a femoral head from an acetabulum, according to an embodiment of the invention.
Figure 7D:
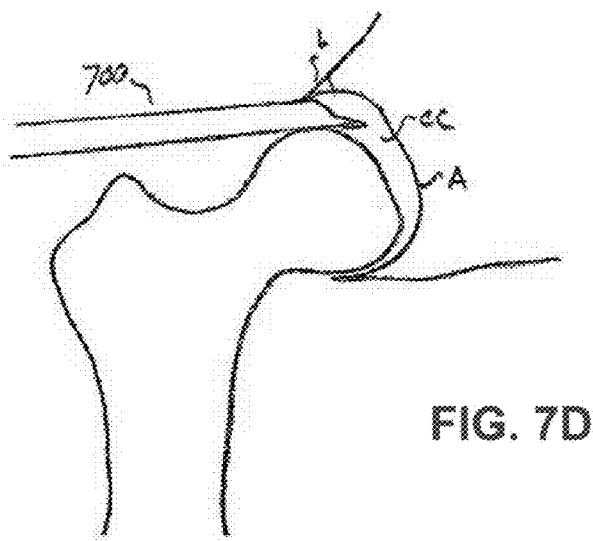
Figure 7E:
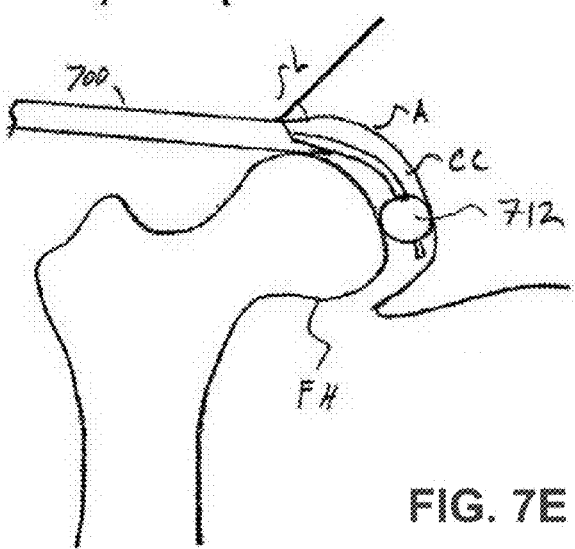

FIGS. 7C-7E show a method for using cannula 700 to provide access to the central compartment CC of a hip joint.

FIG. 7C shows the blade 708 of the cannula 700 being inserted underneath the labrum L. The blade 708 has a compact insertion profile which allows the blade 708 to be inserted under labrum L with little effort. The soft tip 710 can prevent damage to the acetabulum A and femoral head FH. The cannula 700 may then be further inserted into the central compartment CC, as shown in FIG. 7D. The blade 708 and beveled portion 706 slide under labrum L such that the labrum L rests on the outer wall of the cannula 700. Inserting the cannula 700 into the central compartment CC can also at least partially distract the femoral head FH from the acetabulum A.

As shown in FIG. 7E, the cannula 700 can be maintained in position to allow other devices, such as balloon catheter 712, to access the central compartment CC via the lumen of the cannula 700. Balloon catheter 712 can be used to further distract the femoral head FH from the acetabulum A, as shown in FIG. 7E, and the cannula 700 can be optionally removed.

Figure 8A:
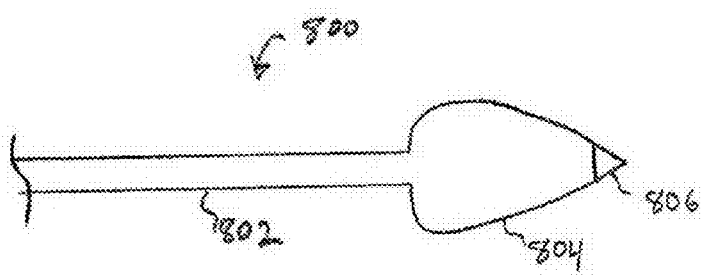
FIGS. 8A and 8B are top and front views, respectively, of a device for providing access to a central compartment of a hip joint, according to an embodiment of the invention.
Figure 8B:
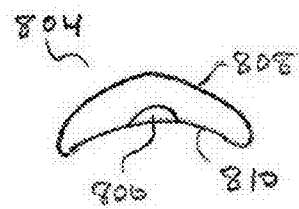
Figure 8C:
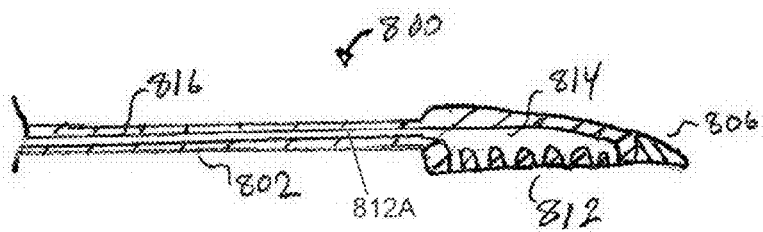
FIG. 8C is a cross-sectional view of the device shown in FIGS. 8A and 8B.

FIGS. 8A-8C show a device 800 for providing access to the central compartment CC of a hip joint.

Device 800 includes a flexible elongate shaft 802 coupled to an expansion device configured as a wedge member 804. Wedge 804 is shaped to gradually taper in thickness to a distal tip 806, which can be constructed from a soft material, (e.g., rubber) to prevent damage to the hip joint during use. The wedge 804 can have a smooth convex top surface 808 shaped to match the surface profile of the acetabulum, and is optionally covered with a soft atraumatic material. The wedge 804 may be formed from a relatively stiff metal or polymer, or may be composed all or partially of a softer compliant material to conform to the shape of the femoral head FH and acetabulum A. The top surface 808 of wedge 804 can include a lubricous coating, such as PTFE or a hydrophilic material. The wedge member 804 can also have a concave bottom surface 810 shaped to match the surface profile of the femoral head FH and/or femoral neck. The bottom surface 810 can be configured to conform to, and adhere to, the femoral head or neck (i.e., to prevent movement of the bottom surface 810 on the femoral head FH), preferably being a flexible and conformable material. For example, the bottom surface 810 can include suction ports, suctions cups, frictional coatings and/or surface treatments, and/or a sticky or adhesive coating. The maximum thickness between the top surface 808 and the bottom surface 810 can range in dimension, e.g., from 4-12 mm. The flexible elongate shaft 802 can be rigid, flexible, or malleable, and either metal or polymer. The flexible elongate shaft 802 can include at least one lumen 812A which is fluidly connected to a suction chamber 814 and suction ports 812 in the wedge 804.

Figure 8D:
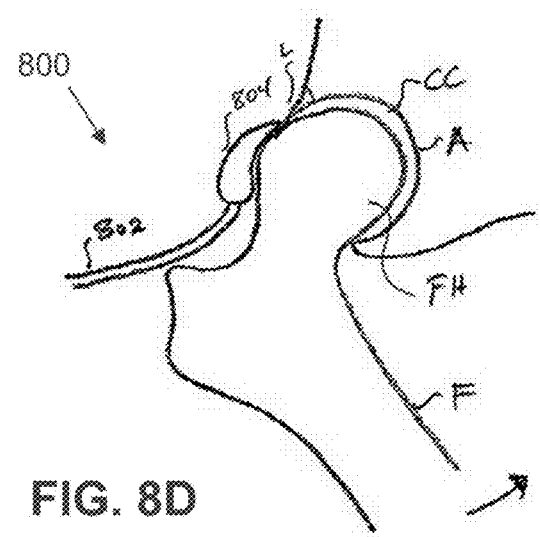
FIGS. 8D-8F are simplified cross-sectional views of a hip joint undergoing a method for accessing a central compartment of a hip joint for distraction of a femoral head from an acetabulum, according to an embodiment of the invention.
Figure 8E:
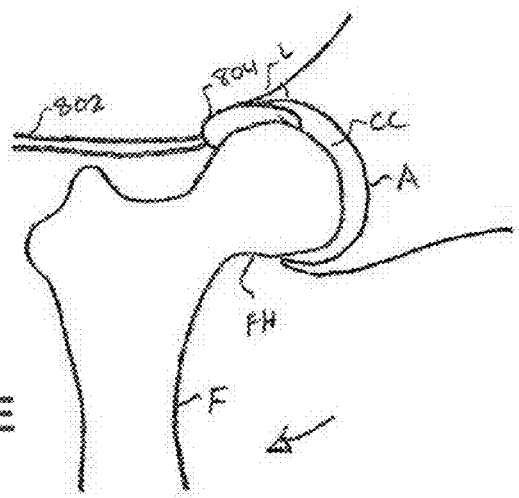
Figure 8F:
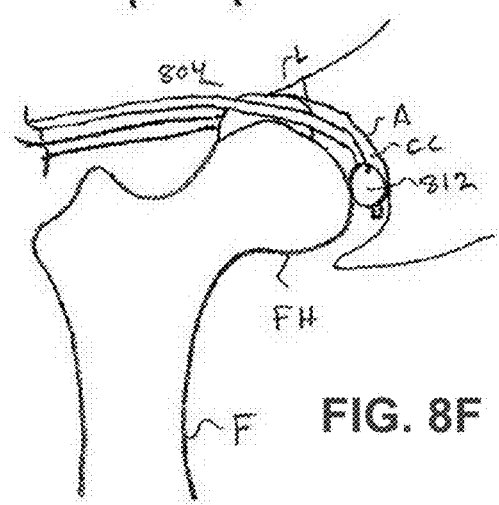

FIGS. 8D-8F show a method for using device 800 to provide access to a central compartment of a hip joint.

In FIG. 8D the femur F is moved rotationally from a normal first position to a rotated second position as shown by the indicative arrow. Accordingly, a portion of the femoral head FH, which is normally covered by the labrum L in the first position, becomes exposed. In FIG. 8D, the shaft 802 is manipulated to position the wedge 804 over the newly exposed portion of the femoral head FH, with the distal tip 806 placed directly adjacent to the bottom edge of the labrum. The bottom surface 810 may be adhered to the newly exposed portion of the femoral head FH using many different techniques, for example, suction, adhesives, or simply relying on the frictional interface between the bottom surface 810 and femoral head FH.

In FIG. 8E the femur F is brought back into its first position while the wedge 804 remains adhered to the femoral head FH, as shown by the indicative arrow. As the wedge 804 is kept in place by adhesion, movement of the femur F forces the distal tip 806 underneath the bottom edge of the labrum L. The adherence of the wedge 804 to the femoral head FH is strong enough to overcome the force placed against the wedge 804 by the labrum L. Femur F may be rotated to, or beyond, its first position, so that the main body of the wedge 804 resides underneath the labrum. Accordingly, the wedge 804 can distract at least a portion of the labrum L and also distract the femoral head FH from the acetabulum A.

In FIG. 8F the wedge 804 is maintained in position to distract the femoral head FH from the acetabulum A sufficiently to allow introduction of other surgical devices into the central compartment CC. For example, a balloon catheter 812 (of the sort as described elsewhere herein) may be inserted into the central compartment CC adjacent to device 800 and inflated at the acetabular fossa AF to further distract the femoral head FH from the acetabulum A, after which the device 800 may be removed.

Figure 9A:
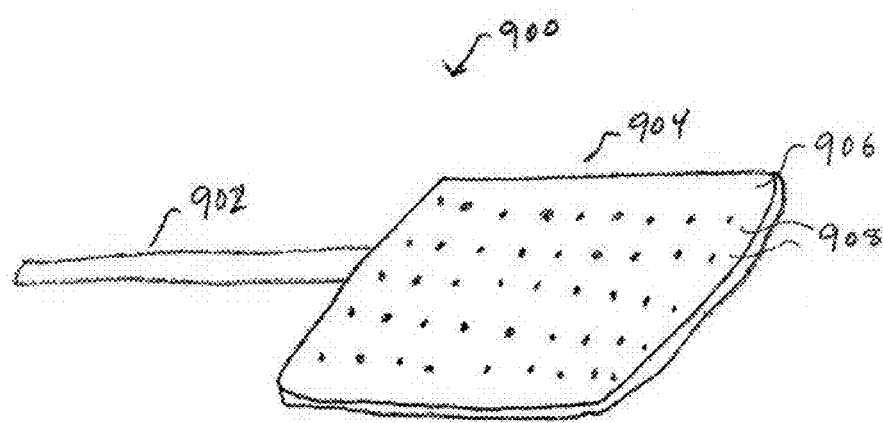
FIGS. 9A and 9B are perspective and cross-sectional views, respectively, of a device for providing access to a central compartment of a hip joint, according to an embodiment of the invention.
Figure 9B:
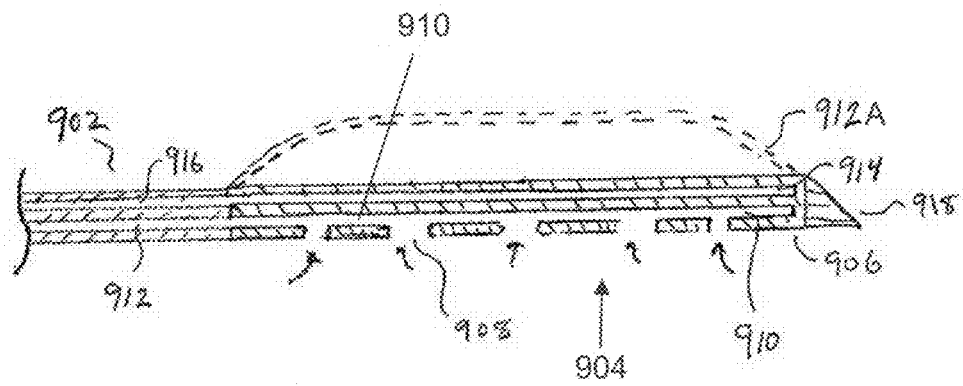

FIGS. 9A and 9B show a device 900 for providing access to the central compartment CC of a hip joint.

Device 900 includes a flexible elongate shaft 902 coupled to an expansion device configured as a blanket 904. The blanket 904 includes an adhering side 906 which can include a surface with a plurality of suction ports 908. Alternatively, the adhering side 906 can include other adhering features, such as suctions cups, frictional coatings, surface treatments, and adhesive coatings. The blanket 908 can be configured to be relatively thin (e.g., less than 0.5 mm) and also be constructed from a flexible material, such as silicone. The blanket 904 is shown as a flat rectangular shape, but can include many other shapes (e.g., round, triangular, etc.) and/or include curvatures. The blanket 904 can have a surface-on-surface laminated construction using sheets of the same or differing material which are bonded together at seams/edges to form one or more internal bladders, thus, the bladders can have an extremely small height when not inflated. The flexible elongate shaft 902 can be constructed similarly to a catheter shaft. The flexible elongate shaft 902 can include at least one lumen which is fluidly connected to suction ports 908.

As shown in FIG. 9B, the blanket 904 can include a first internal chamber 910 which is fluidly connected to the suction ports 908 and to a suction lumen 912 inside the flexible shaft 902. The suction lumen 912 may provide negative air pressure to the suction ports 908, as shown by the indicative arrows. The blanket 904 can include a balloon 912A positioned oppositely to the adhering side 906. The balloon 912A can be configured to be approximately the same uninflated profile as the adhering side 906. A second internal chamber 914 can be fluidly connected to the balloon 912A and to a pressure lumen 916. The pressure lumen 916 can be coupled to a positive fluid pressure source, such as a syringe or hand pump, and provide positive pressure to inflate the balloon 912A, as shown by the dashed lines. The blanket 904 can also include a beveled leading edge 918 which is configured to slide under, and lift, the bottom edge of the labrum L. The leading edge 918 can be constructed from the same material as the blanket 904, or formed from a harder or stiffer material. More than one inflation chamber can be used, for example, a third inflatable chamber may be formed on top of the first internal chamber 910. The third inflatable chamber may also terminate proximate to the beveled leading edge 918 and about a mid-portion of the blanket 904, and thus utilize a stepped construction.

In an alternative embodiment, the blanket 904 can include only one internal chamber, and alternate between providing negative and positive pressure, and accordingly act as both a suction device and a balloon. As a further alternative, the suction ports 908 can be configured to be very small, such that when the blanket 904 is inflated the pressure leakage through the suction ports 908 is minimized and balloon inflation can be maintained. Liquids of higher viscosities may also be used to fill the blanket 904 so as to reduce leakage through the suction ports.

In use, the device 900 is used similarly to device 800 as shown in FIGS. 8D-8F. The adhering surface 906 can be placed on the femoral head FH and moved underneath the labrum L by movement of the femur. The flexibility of the device 900 can allow the device 900 to easily conform to the shape of the femoral head FH when vacuum is applied. Due to a low deflated profile, the blanket 904 slides under the labrum as the femur F is rotated. Once the device 900 has been placed, the balloon 912A can be inflated to distract at least a portion of the labrum L and also distract the femoral head FH from the acetabulum A.

FIGS. 10A-10C show a device 1000 for providing access to the central compartment CC of a hip joint.

As shown in FIGS. 10A-10C, the device 1000 can include a flexible shaft 1002 coupled to an expansion device 1004. The expansion device 1004 can utilize a double balloon construction including a suction balloon 1006 positioned oppositely to an inflation balloon 1008. The expansion device 1004 can have a low-profile shape adapted to conform to the shape of the femoral head and/or neck; as such, the outer surface of the suction balloon 1006 can have a concave surface, and the outer surface of the inflation balloon can have a convex surface. The suction balloon 1006 can have a plurality of suction ports 1010. The suction balloon 1006 can include a self-supporting suction chamber 1012 which is fluidly connected to the suction ports 1010 and a suction lumen 1014 of the shaft 1002. Suction balloon 1006 may be constructed to be very low profile and may be a soft, flexible material, but has sufficient rigidity to remain open when negative pressure is applied so as not to collapse and block suction ports 1010. The suction chamber 1012 can include reinforcement members such as internal ribbing, struts, springs, or stents. Alternatively, the surface of the suction balloon 1006 can be made from a relatively rigid material (e.g., a thick-walled polymer) to support and prevent collapse of the suction chamber 1012, but still be flexible enough to conform over the femoral head. The suction lumen 1014 can be coupled to a negative pressure source to supply negative pressure to the suction chamber 1012 and ports 1010. Shaft 1002 may terminate at the proximal side of the expansion device 1004 or may extend through it or beyond its distal end. The inflation balloon 1008 can be fluidly connected to an inflation lumen 1016 of the shaft 1002. The inflation lumen 1016 can be connected to a positive pressure source to provide positive fluid pressure to inflate the inflation balloon 1008, as shown by the dashed lines. The inflation balloon 1008 can have an inflated shape with a convex outer surface as shown by the dashed lines, and can expand laterally to form a bent mattress-like shape. When the inflation balloon 1008 is not inflated, it can be configured to have a very flat, low profile and/or can be folded or wrapped on shaft 1002.

The device 1000 can include a conical tip 1018. The conical tip 1018 may gradually taper from a larger proximal region to a smaller profile distal tip, which is configured to slide under the bottom edge of the labrum L. The conical tip 1018 can include an exit hole for lumen 1022 which runs throughout the shaft 1002. The lumen 1022 can be configured to accept a slidable guidewire 1024. The conical tip 1018 can be formed from the same material as the expansion device, or from a harder metal or polymer. Alternatively, a wedged tip resembling the shape of a duckbill can be used. The wedged tip can have a concave bottom surface which can have the same profile as the concave surface of the suction balloon 1006. The wedged tip can also have a convex top surface.

In use, the device 1000 is used similarly to device 800 (which was shown in use in FIGS. 8D-8F). The suction balloon 1006 can be placed on the femoral head FH, adhered thereto by applying suction through suction ports 1010, and moved underneath the labrum L by movement of the femur. Once the device 1000 has been placed within the central compartment CC, the inflation balloon 1008 can be inflated to distract the femoral head FH from the acetabulum A.

Figure 10D:
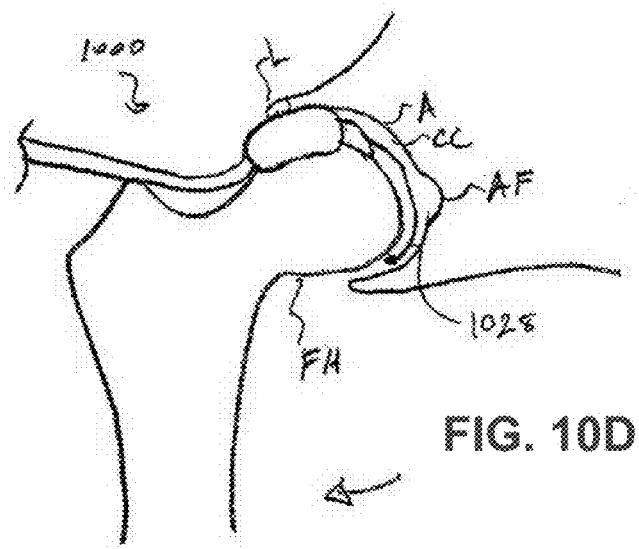
FIGS. 10D-10F are simplified cross-sectional views of a hip joint undergoing a method for accessing a central compartment of a hip joint for distraction of a femoral head from an acetabulum, according to an embodiment of the invention.
Figure 10E:
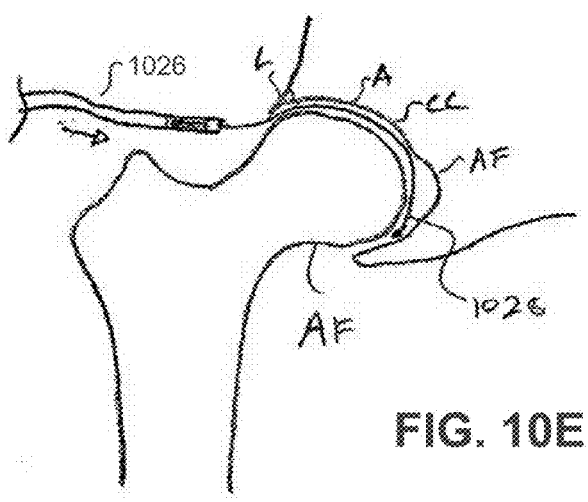
Figure 10F:
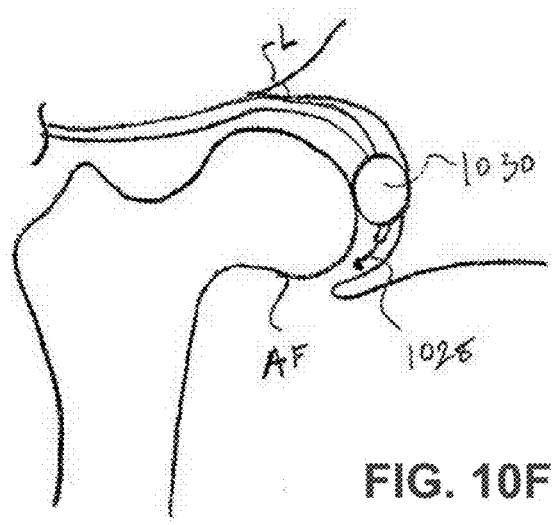

The device 1000 can then be further used as shown in FIGS. 10D-10F.

FIGS. 10D-10F show a method for using device 1000 to provide access to a central compartment CC of a hip joint.

FIG. 10D shows that device 1000 has already been placed in accordance with the above disclosure and the femoral head FH may be separated from the acetabulum A. The guidewire 1028 can be advanced through the lumen 1026 and distally past the wedged tip 1020 and then further into the central compartment CC and past the acetabular fossa AF. Once the guidewire 1028 has been placed, the balloon 1008 may be deflated and the device 1000 may be removed.

FIG. 10E shows that the balloon 1008 has been deflated and the device 1000 removed, while leaving the guidewire 1028 in place. A low profile balloon catheter 1030 having a guidewire lumen is then advanced over the guidewire 1028 as shown by the indicative arrow. The balloon catheter 1030 can then be inserted underneath the labrum L and into the central compartment CC to be inflated at the desired locations (e.g., the acetabular fossa AF), as shown in FIG. 10F. The guidewire 1028 can be removed after the balloon catheter 1030 has been inflated. Inflation of the balloon catheter 1030 can fully distract the femoral head FH from the labrum L, and from the acetabulum A, to provide access to the central compartment CC for other surgical devices.

In alternative embodiments, lumen 1026 has a large enough diameter to allow introduction of the distraction balloon catheter itself through it while the device 1000 remains in place to partially distract the joint. This allows the distraction balloon catheter to be advanced through the space within the joint created by the device 1000.

In the foregoing disclosure, various approaches for distracting a joint are disclosed.

In combination with the foregoing approaches, or as an alternative to the foregoing approaches, additional novel approaches may be used for distracting a joint.

Figure 11:
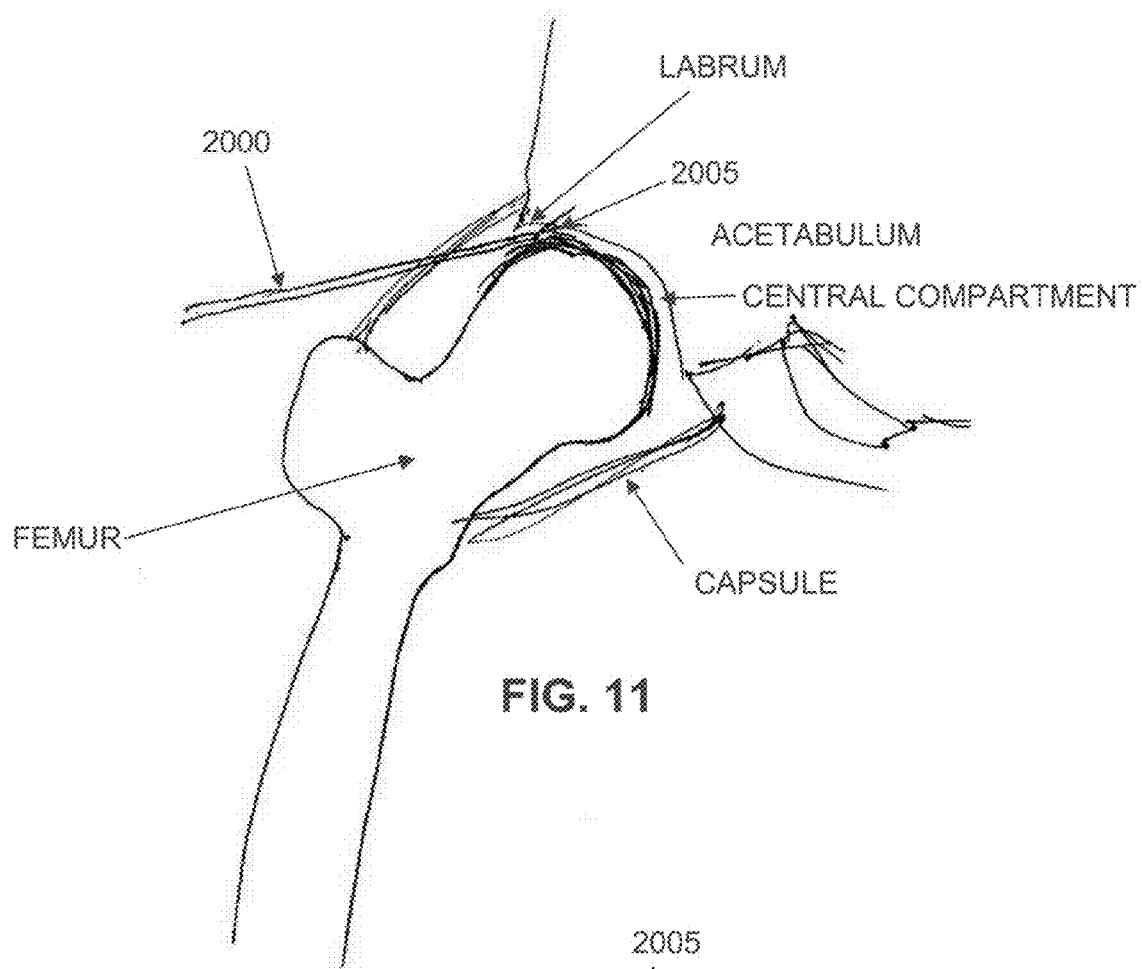
FIGS. 11-16 show additional approaches for creating space within a joint.
Figure 12:
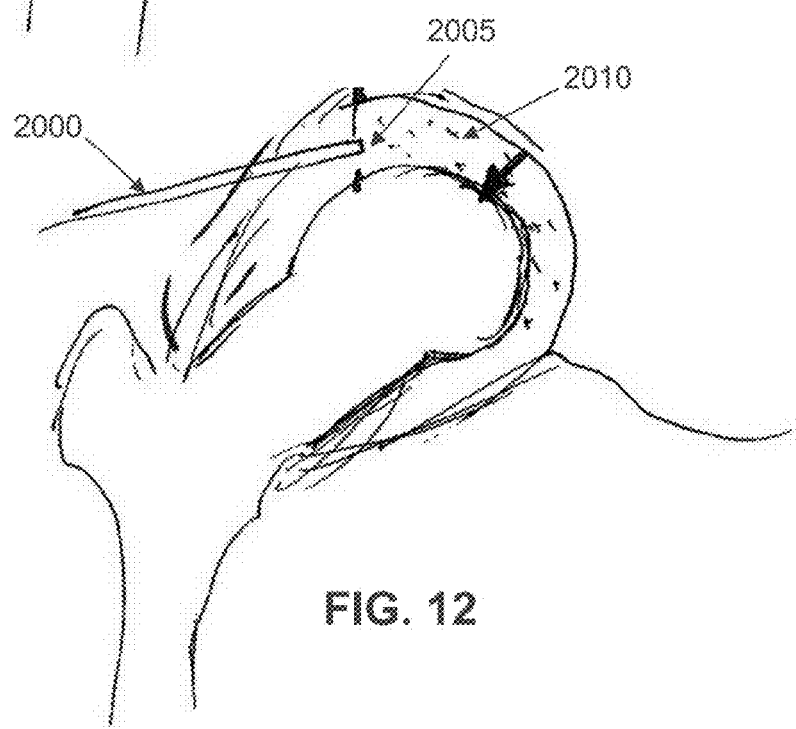

More particularly, and looking now at FIGS. 11 and 12, there is shown a novel approach for facilitating joint distraction. More particularly, in this form of the invention, a cannulated needle, a catheter or another elongated hollow device 2000 is advanced past the capsule and under the labrum so as to enter the central compartment. This may be done by pushing the device 2000 through the capsule and under the labrum, or by cutting open the capsule and then advancing the device 2000 through the opening thereby formed in the capsule and under the labrum. In either case, once the distal tip 2005 of the device 2000 is disposed in the central compartment, a fluid 2010 (e.g., a liquid such as saline or water, a gas such as air, etc.) is advanced (e.g., flushed in the case of a fluid, injected in the case of a gas, etc.) under pressure into the central compartment so as to break suction seal normally established by the labrum.

The fluid is preferably flushed/injected into the central compartment with sufficient force that a small gap is created between the femoral head and acetabulum (see FIG. 11, which shows the position of the joint prior to introduction of the fluid, and FIG. 12, which shows the position of the joint after the fluid is introduced into the joint under pressure). A balloon catheter of the sort disclosed above may then be advanced into the central compartment and inflated so as to further distract the joint.

Alternatively, once the flushing/injection of fluid breaks the suction seal normally established by the labrum, external traction can be applied to the leg so as to create a gap large enough to receive the balloon. It will be appreciated that in this form of the invention, a lighter amount of traction force will be required since the suction seal will already have been broken.

Yet another embodiment of the invention provides a method for providing access to the hip joint similar to that shown in FIG. 11 but by first pressurizing the peripheral compartment of the hip joint to a high pressure. Then the seal of labrum may be compromised using a needle or similar tube made out of metal or a polymer. This will create a leak from the high pressure of the peripheral compartment to the low pressure in the central compartment, thus creating a path for the fluid to flow into the central compartment. This will create a small gap between the femoral head and acetabulum. As explained above, a distraction balloon can then be used to create further distraction.

Figure 13:
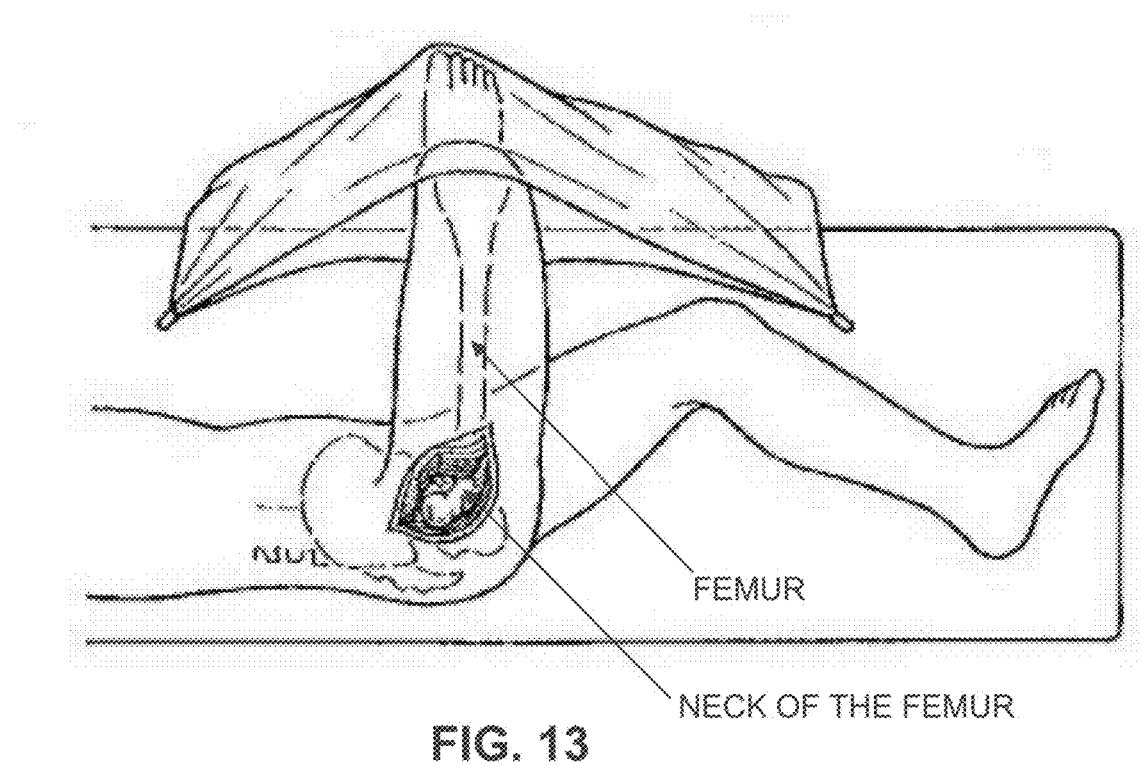

In another form of the invention, and looking now at FIG. 13, the patient's leg is flexed and then rotated internally. This action creates a space between the head of the femur and the acetabulum at the periphery where the bones would normally be in contact. A balloon catheter may then be deployed into this space. The balloon catheter may then be inflated to create distraction space. To assist moving the balloon catheter into the joint, the leg may now be extended and/or externally rotated while pushing the balloon catheter into the space. Once the balloon catheter is in the desired location, the balloon (of any of the types previously disclosed) can be inflated, creating the desired distraction. The surgeon can then manipulate the leg to any position appropriate for the intended surgical treatment.

Figure 14:
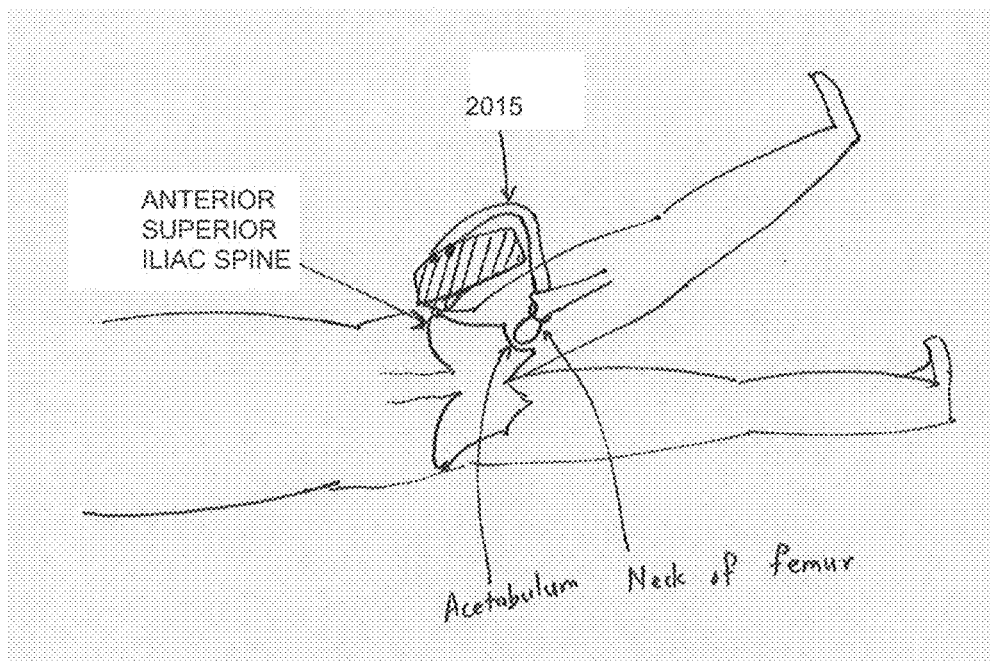
Figure 15:
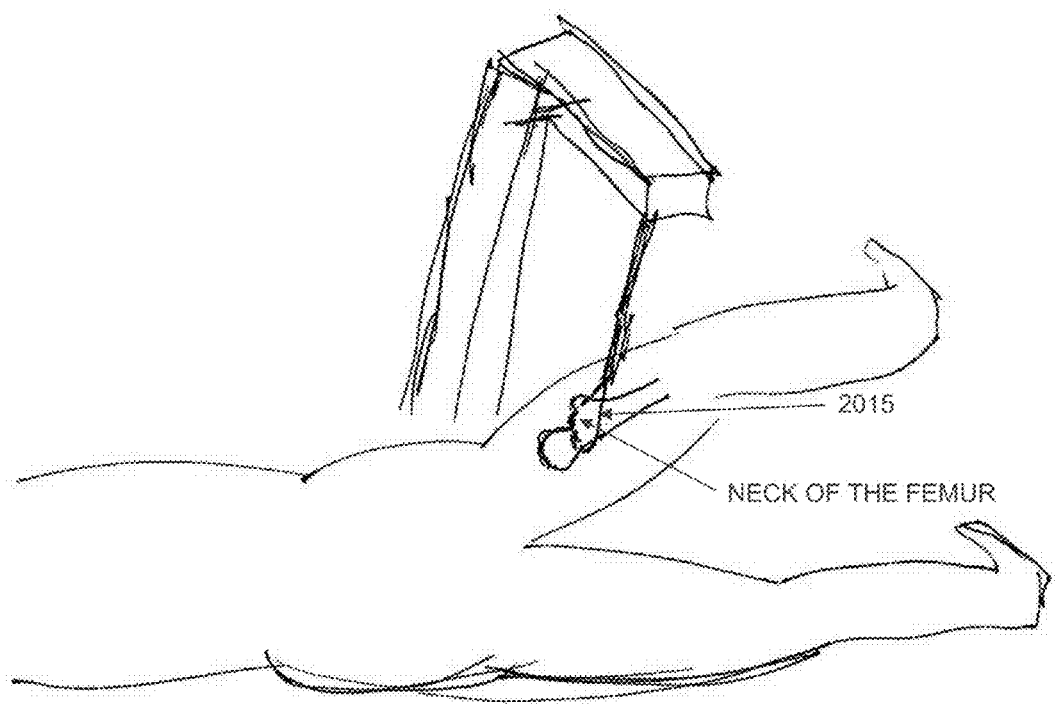

And in still another form of the invention, and looking now at FIGS. 14 and 15, the patient is positioned in a lateral decubitus position. Then a loop 2015 (e.g., suture, wire, etc.) is passed through the skin and positioned around the femoral neck. Next, tension is applied to the loop 2015 so as to separate the femoral head from the acetabulum and create a gap therebetween. The gap may be created by using an external device which rests on the Anterior Superior Iliac Spine (ASIS), as shown in FIG. 14. Or the gap may be created using a standing device, as shown in FIG. 15. Finally, a balloon catheter is advanced into the gap between the femoral head and the acetabulum, and the balloon inflated so as to further distract the joint. If desired, the suction seal of the labrum may be broken before mechanical distraction, e.g., as discussed above and shown in FIGS. 11 and 12.

In yet another embodiment, the weight of the patient's body may be used to supply the force to dislocate the hip. As above, with the patient in a lateral position, the leg for distraction may be held fixated by means of a sling, clamp or other means. The patient may be resting on a table that may be lowered relative to the apparatus holding the leg, thereby creating relative displacement of the femoral head out of the acetabulum. This is analogous to the tension drawn in the leg by current surgical practices, however, it uses the weight of the patient to generate the tension. Once sufficient tension is created and the hip is dislocated, the balloon catheter may be introduced, balloon inflated and the table may be raised. Also, as an alternative to drawing full surgical distraction on the hip through the external means, the external traction may be used to only create sufficient space that the balloon catheter may need to be introduced, then the balloon is inflated and the external traction removed. An addition benefit of this external traction method is that it does not rely upon a perineal post for creating distraction, thereby relieving stresses and injuries in that area that are found in the current external distraction methods. Also, in this method, other joints such as knee and ankle are not distracted as with conventional external distraction methods.

Figure 16:
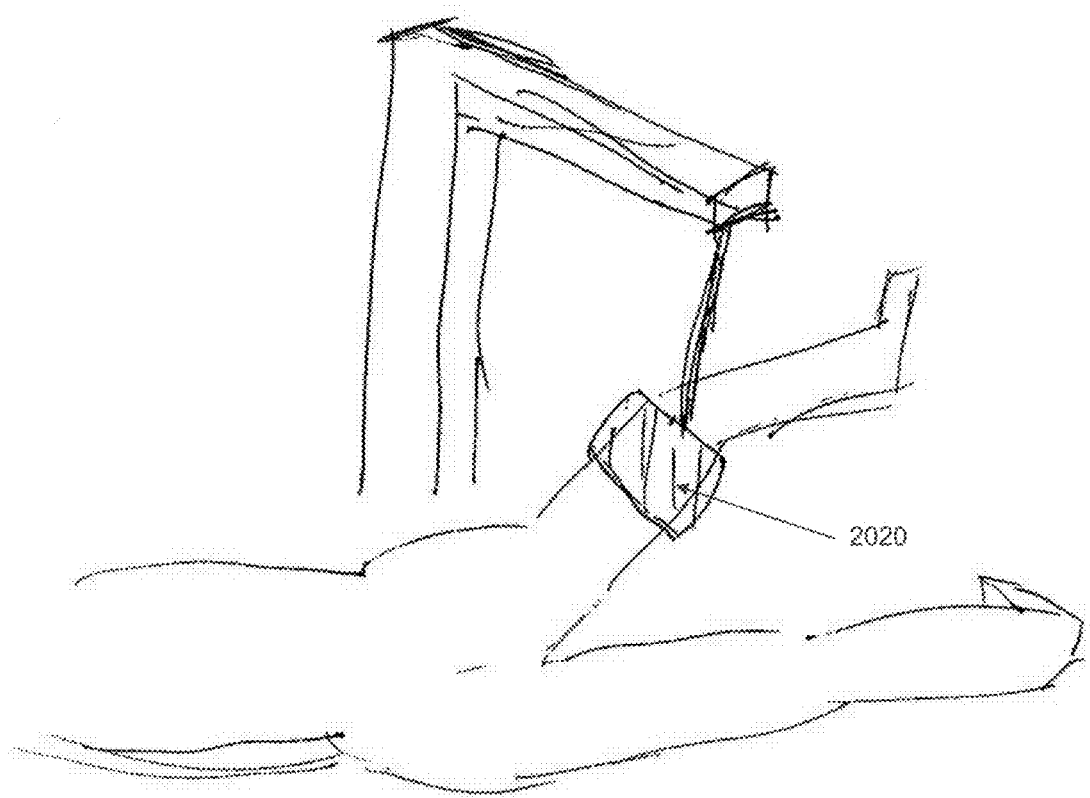

As an alternative to the foregoing, and looking now at FIG. 16, an external clamp or sling 2020 may be secured to the leg just above the knee. Tension is then applied to the clamp/sling 2020 so as to separate the femoral head from the acetabulum. A balloon catheter is thereafter advanced into the gap between the femoral head and the acetabulum, and the balloon inflated so as to further distract the joint. Again, if desired, the suction seal of the labrum may be broken before mechanical distraction, e.g., such as discussed above and shown in FIGS. 11 and 12.

Use of the Present Invention for Other Applications

It should be appreciated that the present invention may be used for distracting the hip joint in an open, more invasive procedure as well as in a minimally invasive procedure.

The present invention can also be used in addressing hip joint pathologies where joint distraction is not needed but space creation is needed.

Furthermore, the present invention may be used for distracting or otherwise treating joints other than the hip joint, e.g., it may be used to distract the shoulder, ankle or elbow joints.

Modifications

While exemplary structures and methods have been described in some detail, by way of example and for clarity of understanding, a variety of changes, adaptations, and modifications will be obvious to those of skill in the art. Hence, the scope of the present invention is limited solely by the appended claims.

What is claimed is:

1. A method for distracting a femoral head from an acetabulum of a hip joint, the method comprising:
   inserting a first catheter having a first balloon into a central compartment of the hip joint between the femoral head and the acetabulum, the first balloon having a first size;
   inflating the first balloon of the first catheter to distract the femoral head from the acetabulum a first distance;
   using the first balloon of the first catheter to maintain distraction between the femoral head and the acetabulum by the first distance, and advancing a second catheter over a shaft of the first catheter so that a second balloon on the second catheter is disposed in the first distance between the distracted femoral head and the acetabulum, wherein the second balloon is placed in the acetabular fossa of the acetabulum, the acetabular fossa being a recessed region in the joint surface of the acetabulum, the second balloon having a second size, wherein the second size is greater than the first size; and
   inflating the second balloon on the second catheter to further distract the femoral head from the acetabulum a second distance, wherein the second distance is greater than the first distance.

2. The method of claim 1, wherein the first distance is 2-4 mm.

3. The method of claim 2, wherein the second distance is about 4-12 mm.

4. The method of claim 1, additionally comprising lifting up a labrum of the hip joint using the first catheter.

5. The method of claim 1, additionally comprising: removing the first catheter while leaving the inflated second balloon in place.

* * * * *